(12) United States Patent
Barton et al.

(10) Patent No.: US 8,766,017 B2
(45) Date of Patent: *Jul. 1, 2014

(54) INTEGRATED PROCESS FOR THE PREPARATION OF 1,4-CYCLOHEXANEDIMETHANOL FROM TEREPHTHALIC ACID

(75) Inventors: Benjamin Fredrick Barton, Kingsport, TN (US); Steven Leroy Cook, Kingsport, TN (US); Jeff Scott Howell, Jonesborough, TN (US); Noah Glenn McMillan, Kingsport, TN (US); Damon Bryan Shackelford, Kingsport, TN (US); Brent Alan Tennant, Church Hill, TN (US); Phillip Wayne Turner, Blountville, TN (US)

(73) Assignee: Eastman Chemical Company, Kingsport, TN (US)

( * ) Notice: Subject to any disclaimer, the term of this patent is extended or adjusted under 35 U.S.C. 154(b) by 210 days.

This patent is subject to a terminal disclaimer.

(21) Appl. No.: 13/194,040

(22) Filed: Jul. 29, 2011

(65) Prior Publication Data

US 2013/0030220 A1   Jan. 31, 2013

(51) Int. Cl.
C07C 35/08 (2006.01)

(52) U.S. Cl.
USPC ........................................................ 568/822

(58) Field of Classification Search
None
See application file for complete search history.

(56) References Cited

U.S. PATENT DOCUMENTS

| | | | |
|---|---|---|---|
| 1,628,190 A | 5/1927 | Raney | |
| 3,334,149 A | 8/1967 | Akin et al. | |
| 5,185,476 A | 2/1993 | Gustafson | |
| 5,387,752 A | 2/1995 | Scarlett et al. | |
| 5,395,987 A | 3/1995 | Rathmell et al. | |
| 5,399,742 A | 3/1995 | Tennant et al. | |
| 6,187,968 B1 | 2/2001 | Itoh et al. | |
| 6,284,703 B1 | 9/2001 | Ostgard et al. | |
| 6,919,489 B1 | 7/2005 | McCusker-Orth | |
| 7,632,962 B2 | 12/2009 | Liu | |
| 8,410,317 B2 * | 4/2013 | Turner et al. | 568/822 |
| 8,410,318 B2 * | 4/2013 | Barton et al. | 568/822 |

FOREIGN PATENT DOCUMENTS

| | | |
|---|---|---|
| GB | 988316 A | 4/1965 |
| JP | 2000/001447 A | 1/2000 |

OTHER PUBLICATIONS

Co-pending U.S. Appl. No. 13/194,024, filed Jul. 29, 2011, Phillip Wayne Turner, et al.
Co-pending U.S. Appl. No. 13/194,051, filed Jul. 29, 2011, Benjamin Fredrick Barton, et al.
Co-pending U.S. Appl. No. 13/476,219, filed May 21, 2012, Benjamin Fredrick Barton, et al.
USPTO Office Action dated Jun. 28, 2012 for co-pending U.S. Appl. No. 13/194,051.
USPTO Office Action dated Jun. 29, 2012 for co-pending U.S. Appl. No. 13/194,024.
Notification of Transmittal of the International Search Report and the Written Opinion of the International Searching authority with a mailing date of Sep. 6, 2012, International Application No. PCT/US2012/047792.
Notification of Transmittal of the International Search Report and the Written Opinion of the International Searching authority with a mailing date of Sep. 6, 2012, International Application No. PCT/US2012/047793.
Notification of Transmittal of the International Search Report and the Written Opinion of the International Searching authority with a mailing date of Sep. 11, 2012, International Application No. PCT/US2012/047795.
Notification of Transmittal of the International Search Report and the Written Opinion of the International Searching authority with a mailing date of Sep. 11, 2012, International Application No. PCT/US2012/047796.

* cited by examiner

Primary Examiner — Sudhakar Katakam
(74) Attorney, Agent, or Firm — Eric D. Middlemas; Louis N. Moreno

(57) ABSTRACT

Disclosed is an integrated process for the preparation of 1,4-cyclohexanedimethanol from terephthalic acid. Terephthalic acid is esterified with (4-methylcyclohexyl)methanol and the terephthalate ester hydrogenated to 1,4-cyclohexanedimethanol in a 2-stage process. The (4-methylcyclohexyl)methanol that is formed during the hydrogenation step is recycled to the esterification reaction. Also disclosed is a method for purifying and recovering the 1,4-cyclohexanedimethanol product.

23 Claims, No Drawings

INTEGRATED PROCESS FOR THE PREPARATION OF 1,4-CYCLOHEXANEDIMETHANOL FROM TEREPHTHALIC ACID

FIELD OF THE INVENTION

This invention pertains to an integrated process for the preparation of 1,4-cyclohexanedimethanol by esterification of terephthalic acid and the subsequent catalytic hydrogenation of the terephthalate diester. More particularly, this invention pertains to a process for the preparation of 1,4-cyclohexanedimethanol in which the by-products of the hydrogenation process are recycled as raw materials for the preparation of the terephthalate diester feedstock and in which the purification of the 1,4-cyclohexanedimethanol product is simplified.

BACKGROUND OF THE INVENTION

Cyclohexanedimethanols are important intermediates for producing a variety of polyesters for coatings, fibers, molding plastics, packaging materials, and the like. Cyclohexanedimethanols are typically manufactured by the hydrogenation of the corresponding cyclohexanedicarboxylate esters. For example, one of the more commercially important cyclohexanedimethanols, 1,4-cyclohexanedimethanol (abbreviated herein as "CHDM"), typically is prepared by a two-step hydrogenation process involving hydrogenation of dimethyl terephthalate (abbreviated herein as "DMT"), to give dimethyl 1,4-cyclohexanedicarboxylate (abbreviated herein as "DMCD"), followed by hydrogenation of the ester groups. The various steps of this process have been described, for example, in U.S. Pat. Nos. 3,334,149; 6,919,489; 5,399,742; 5,387,752; 5,395,987; 5,185,476; and 7,632,962; and United Kingdom Patent Application No. 988,316.

The use of DMT as starting material for the preparation of CHDM presents several challenges. DMT is typically prepared by the esterification of terephthalic acid with methanol under high pressures and temperatures that requires expensive, specialized process equipment and can result in increased energy consumption and operating costs. Further, during the esterification process, DMT tends to form solids within the reflux zones of the process, which can cause plugging and reduce the efficiency of the heat exchange surfaces. Other solvents such as, for example, xylene may be introduced in the reflux zone to help liquify the DMT, but this solution places additional purification requirements on the DMT process. DMT must also be distilled prior to its introduction into the hydrogenation step of the CHDM process in order to remove partial esterification products and any esterification catalysts that can poison and/or reduce the activity of the downstream hydrogenation catalysts. Finally, the hydrogenation of DMT releases methanol that requires additional purification and processing steps in order to recover and recycle the methanol from the CHDM hydrogenation product mixtures. The use of alternative CHDM feedstocks that avoid these difficulties, therefore, could greatly improve the efficiency and reduce the equipment and processing costs of the CHDM process.

SUMMARY OF THE INVENTION

It has been discovered that 1,4-cyclohexanedimethanol may be efficiently prepared in a simplified process that comprises the preparation of the bis(4-methy-cyclohexyl)methanol diester of terephthalic acid followed by hydrogenation of this ester to produce the CHDM. One embodiment of our invention, therefore, is a process for the preparation of 1,4-cyclohexanedimethanol from terephthalic acid comprising:

(i). contacting terephthalic acid and (4-methylcyclohexyl) methanol in a mole ratio of alcohol to acid of at least 2:1, in a reaction zone at a temperature of about 200° C. to about 300° C. under superatmospheric pressure, while removing water from the reaction zone, to form an esterification product mixture comprising bis(4-methylcyclohexyl)methyl)terephthalate and unreacted (4-methylcyclohexyl) methanol;

(ii). contacting the esterification product mixture with hydrogen in a first hydrogenation zone in the presence of a catalyst effective for hydrogenation of an aromatic ring to produce a liquid effluent comprising bis(4-methylcyclohexyl)-methyl)cyclohexane-1,4-dicarboxylate;

(iii). contacting the effluent from the first hydrogenation zone with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol that was present in the esterification product mixture, released during the hydrogenation of the bis(4-methylcyclohexyl)methyl)cyclohexane-1,4-dicarboxylate, and additionally produced as a by-product and;

(iv) recycling at least a portion of the (4-methylcyclohexyl) methanol from step (iii) to step (i).

In the process of the invention, terephthalic acid is esterified with (4-methylcyclohexyl)-methanol (abbreviated herein as "MCHM"), which is a by-product of the CHDM hydrogenation process, to produce bis(4-methylcyclohexyl)methyl) terephthalate that is then hydrogenated to CHDM. The MCHM released during the ester hydrogenation step, therefore, does not introduce any new impurities into the hydrogenation process and can be recycled to the esterification step of the process.

Our inventive process also provides a simplified method of purification of the CHDM hydrogenation product mixture. Thus, another embodiment of the invention is a process for the preparation of 1,4-cyclohexanedimethanol, comprising:

(i). contacting bis(4-methylcyclohexyl)methyl) terephthalate with hydrogen in a first hydrogenation zone in the presence of a catalyst effective for hydrogenation of an aromatic ring to produce a liquid effluent comprising bis(4-methylcyclohexyl)-methyl)cyclohexane-1,4-dicarboxylate;

(ii). contacting the effluent from the first hydrogenation zone with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol;

(iii). distilling the hydrogenation product from step (ii) to recover a distillate comprising a majority of the (4-methylcyclohexyl)methanol in the hydrogenation product and a distillation bottoms comprising a majority of the 1,4-cyclohexanedimethanol and 4,4'-oxybis(methylene)bis(methylcyclohexane) in the hydrogenation product;

(iv). allowing the distillation bottoms to form a lower layer comprising a majority of the 1,4-cyclohexanedimethanol in the distillation bottoms and a upper layer comprising a majority of the 4,4'-oxybis(methylene)bis(methylcyclohexane) in the distillation bottoms; and (v). separating the upper and lower layers of step (iv) and recovering the 1,4-cyclohexanedimethanol from the lower layer by distillation.

After removal of at least a portion of the MCHM present in the crude CHDM hydrogenation mixture, the distillation bottoms separates into an upper layer containing the diether of MCHM and many of the impurities present in the hydrogenation product and a lower layer comprising most of the CHDM product. Most of the by-products produced during the hydrogenation step, therefore, can be removed by a simple separation of the upper and lower layers.

The esterification and purification steps of our process can be combined to provide an integrated process for CHDM in which the MCHM by-product from the hydrogenation step is recycled to the TPA esterification step as the alcohol feedstock. Yet another aspect of the invention, therefore, is a process for the preparation of a 1,4-cyclohexanedimethanol from terephthalic acid, comprising:

(i). contacting terephthalic acid and (4-methylcyclohexyl) methanol in a mole ratio of alcohol to acid of at least 2:1, in a reaction zone at a temperature of about 200° C. to about 300° C. under superatmospheric pressure, while removing water from the reaction zone, to form an esterification product mixture comprising bis(4-methylcyclohexyl)methyl)terephthalate and unreacted (4-methylcyclohexyl) methanol;

(ii). contacting the esterification product mixture with hydrogen in a first hydrogenation zone in the presence of a catalyst effective for hydrogenation of an aromatic ring to produce a liquid effluent comprising bis(4-methylcyclohexyl)-methyl)cyclohexane-1,4-dicarboxylate;

(iii). contacting the effluent from the first hydrogenation zone with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol;

(iv). distilling the hydrogenation product from step (iii) to recover a distillate comprising a majority of the (4-methylcyclohexyl)methanol in the hydrogenation product and a distillation bottoms comprising a majority of the 1,4-cyclohexanedimethanol and 4,4'-oxybis(methylene)bis(methylcyclohexane) in the hydrogenation product;

(v). allowing the distillation bottoms to form an lower layer comprising a majority of the 1,4-cyclohexanedimethanol in the distillation bottoms and a upper layer comprising a majority of the 4,4'-oxybis(methylene)bis(methylcyclohexane) in the distillation bottoms;

(vi). separating the upper and lower layers of step (iv) and recovering the 1,4-cyclohexanedimethanol from the lower layer by distillation; and (vii) recycling at least a portion of the (4-methylcyclohexyl) methanol from step (iv) to step (i).

DETAILED DESCRIPTION

The present invention provides a process for the preparation of 1,4-cyclohexanedimethanol by esterifying terephthalic acid (abbreviated herein as "TPA") with (4-methylcyclohexyl)methanol ("MCHM") and hydrogenating this ester to CHDM. In a general embodiment, the invention provides a process for the preparation of 1,4-cyclohexanedimethanol from terephthalic acid comprising:

(i). contacting terephthalic acid and (4-methylcyclohexyl) methanol in a reaction zone at a temperature of about 200° C. to about 300° C. under superatmospheric pressure, while removing water from the reaction zone, to form an esterification product mixture comprising bis(4-methylcyclohexyl)methyl) terephthalate, (ii). contacting the esterification product mixture with hydrogen in a first hydrogenation zone in the presence of a catalyst effective for hydrogenation of an aromatic ring to produce a liquid effluent comprising bis(4-methylcyclohexyl)-methyl)cyclohexane-1,4-dicarboxylate;

(iii). contacting the effluent from the first hydrogenation zone with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol, and;

(iv). recycling at least a portion of the (4-methylcyclohexyl) methanol from step (iii) to step (i).

The MCHM used as a starting material for our process is produced as a by-product in the production of 1,4-cyclohexanedimethanol. Thus, because the esterification process does not introduce any new materials (e.g., methanol to make dimethyl terephthalate) into the overall CHDM process, our novel process reduces the amount equipment needed for the preparation of 1,4-cyclohexanedimethanol from terephthalic acid and simplifies the purification of the final product. The process of the invention also can be used for the preparation of 1,3-cyclohexanedimethanol from isophthalic acid.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "C1 to C5 hydrocarbons," is intended to specifically include and disclose C1 and C5 hydrocarbons as well as C2, C3, and C4 hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the claims, the singular forms "a," "an" and "the" include their plural referents unless the context clearly dictates otherwise. For example, reference to a "promoter" or a "reactor" is intended to include the one or more promoters or reactors. References to a composition or process containing or including "an" ingredient or "a" step is intended to include other ingredients or other steps, respectively, in addition to the one named.

The terms "containing" or "including," are synonymous with the term "comprising," and is intended to mean that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

The esterification step of our process comprises contacting terephthalic acid with MCHM in a reaction zone, under elevated temperatures and pressures, and removing the water produced in the esterification from the reaction zone as the reaction progresses. The molar ratio of alcohol to acid that can be used is typically at least 2:1. For example, the ratio of MCHM to terephthalic acid can be about 2:1 to about 10:1. Some additional examples of molar ratios of alcohol to acid in the esterification step include about 2:1 to about 9:1; about 2:1 to about 8:1; about 2:1 to about 7:1; about 2:1 to about 5:1; about 2:1 to about 4:1; and about 2:1 to about 3:1.

It is advantageous to remove the water produced by the esterification reaction in order to improve the rate of the reaction and the conversion to the terephthalic acid diester. Removal of the water may be accomplished by any conventional means known to persons skilled in the art such as, for example, by distillation, membrane separation, the use of absorbents, or combinations thereof. For example, the water of reaction may be removed by simple distillation from the esterification reaction or by azeotropic distillation with MCHM. With azeotropic distillation, the MCHM/water azeotrope is allowed to separate into an MCHM layer and a water layer, the water layer removed, and the MCHM layer returned to the esterification reaction. In another example, the water of the reaction can be removed by azeotropic distillation by adding a solvent to the esterification reaction mixture that forms an azeotrope with water under the esterification conditions of temperature and pressure. The use of azeotropic solvents, however, will, in general, require additional steps to remove the azeotropic solvent from either the esterification or CHDM reaction product mixture. The water of reaction may also be removed by exposing or passing the reaction mixture through an adsorbent. The removal of the water of reaction from the reaction zone also may be assisted by passing an inert gas through the TPA-MCHM reaction mixture in the reaction zone and condensing the water from the inert gas stream after it exits the reactor. Nitrogen is an example of an appropriate inert gas. The inert gas typically is fed below the surface of the TPA-MCHM reaction mixture by means of a conventional conduit or via a gas sparging device. The inert gas may be fed intermittently or discontinuously. For example, the inert gas can be fed continuously at the commencement of the esterification reaction. The amount of gas passed through the TPA-MCHM reaction mixture may vary significantly but typically is in the range of about 2 to 5 volumes of gas per volume of reaction mixture per hour. It will be apparent to persons skilled in the art that numerous variations and combinations of these methods are possible.

The esterification may be carried out by the joint addition of the TPA and MCHM or by the incremental addition of one of the feed substrate materials to the other. For example, the terephthalic acid can be added incrementally to a reaction zone that contains the full amount of the alcohol to be used in the esterification reaction. Alternatively, the MCHM may be added incrementally to the full or partial amount of TPA that is to be used in the esterification process. The term "incrementally," as used herein, is intended to have its plain meaning of adding the TPA component or MCHM component to the reaction zone in one or more increments or portions to increase the amount of the MCHM or TPA component in the reaction zone. The increments do not have to be equal in size. For example, one increment may contain 90% of the total amount of TPA component and a second increment may contain the remaining 10%. The increments may be added stepwise in discrete portions, continuously, or in a combination thereof. Therefore, the term "incrementally," as used in the description and claims, is intended to include both continuous and stepwise additions of the MCHM and/or TPA components. Thus, "incrementally" means that, over the duration of the entire process, the MCHM or TPA components can be added to the reaction zone continuously, stepwise in 2 or more stages or discrete steps, or in a combination of continuous and stepwise addition. Thus, in one embodiment of the invention, the TPA component is added to the reaction zone in 2 or more stages. In another embodiment, the TPA component is added to the reaction zone continuously.

The TPA and MCHM are contacted in a reaction zone at a temperature of about 200 to about 300° C. under superatmospheric pressure. For example, the TPA and MCHM can be contacted at a temperature of about 220 to about 280° C. at a pressure of about 1.4 bar gauge to about 50 bar gauge. Other examples of pressure and temperature that the esterification step may be operated at about 230 to about 280° C. at a pressure of about 1.4 to about 21 bar gauge, and about 240 to about 270° C. at about 1.4 to about 6.9 bar gauge.

The TPA and MCHM are reacted while removing water from the reaction mixture to form an esterification product mixture comprising bis(4-methylcyclohexyl)-methyl)terephthalate, represented by formula (I), and unreacted (4-methylcyclohexyl)-methanol. In one embodiment of the process, the TPA and MCHM are heated together with water removal until a product mixture having a desired conversion is obtained.

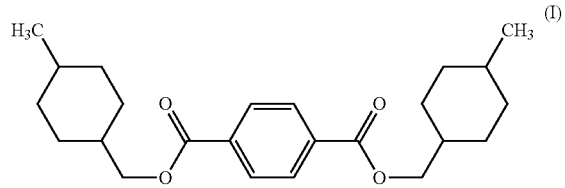 [SMILES: CC1CCC(COC(=O)c2ccc(C(=O)OCC3CCC(C)CC3)cc2)CC1]

(I)

The desired conversion can be determined by conventional analytical methods known to persons skilled in the art such as, for example, by NMR, titration (i.e., acid number), gas chromatography, and liquid chromatography. Acid number may be determined by titration of the esterification product mixture with potassium hydroxide and is reported as mg of potassium hydroxide consumed for each gram of esterification product mixture (mg KOH/g esterification product mixture). The esterification product mixture will typically have an acid number of about 10 mg KOH or less/gram of esterification product mixture to reduce poisoning and deactivation of any hydrogenation catalysts in the subsequent steps of the process. Additional examples of acid number values for the esterification product mixture are about 8 mg KOH or less/gram of esterification product mixture, about 5 mg KOH or less, and about 3 mg KOH or less. The esterification step may also be monitored by measuring the water evolved from the reaction mixture, computer modeling of the reaction rate, or any other means capable of determining the concentration of reactants or products in the esterification product mixture.

The MCHM used to esterify TPA in the process of the invention is produced as a by-product in the production of CHDM by the multistage hydrogenation of TPA diesters that proceeds by hydrogenation of the aromatic ring produce the corresponding 1,4-cyclohexanedicarboxylate diester, which is further hydrogenated to produce CHDM. In one embodiment of our invention, therefore, the MCHM used in the esterification reaction with TPA can be recovered and recycled from a process for the preparation of CHDM by hydrogenation of bis(4-methylcyclohexyl)methyl) terephthalate. The MCHM used in the esterification may also include unreacted MCHM that has been recovered and recycled from the esterification step of our CHDM process. In one embodiment of our invention, the MCHM used to esterify TPA, recycled to the esterification step, or a combination thereof, further comprises one or more additional alcohols having 4 to 20 carbon atoms in minor or major quantities. In another embodiment, the one or more additional alcohols comprise 1-butanol, 2-butanol, 2-ethylhexanol, cyclohexanol, benzyl alcohol, 1-hexanol, 1-pentanol, 1-octanol, 1-nonanol, 1-decanol, or combinations thereof. In yet another embodiment, the MCHM used to esterify TPA in step (i) contains from 0 to than 5 weight percent of the one or more additional alcohols based on the total amount of MCHM used in the esterification step. Some other examples of the concentration of the additional alcohols are 0 to less than 3 weight percent, 0 to less than 2 weight percent, 0 to less than 1 weight percent, and 0 to less than 0.5 weight percent. In still another embodiment, the MCHM used to esterify TPA in step (i) contains greater than 10 weight percent of one or more additional alcohols based on the total amount of MCHM used in the esterification step.

The esterification reaction may be carried out in the presence or absence of an exogenous esterification catalyst, i.e., a catalyst other than terephthalic acid that is added to the reaction mixture for the purpose of increasing the rate of the esterification reaction. Any esterification catalyst that is known in art may be used. For example, the TPA and MCHM can be contacted in the presence of a catalyst comprising compounds of titanium, magnesium, aluminum, boron, silicon, tin, zirconium, zinc, antimony, manganese, calcium, vanadium, sulfuric acid, p-toluene sulfonic acid, methane sulfonic acid, or phosphoric acid. For example, acetates, chlorides, nitrates, sulfates, oxides and alkoxides of metals such as zinc, manganese, tin, titanium, antimony, cobalt and lithium may be used. Buffering compounds, such as alkaline salts of organic acids, can be included with the catalysts if desired.

Some representative examples of catalysts that may be used in the esterification step include, but are not limited to, titanium, zirconium, and tin alcoholates, carboxylates, and chelates; zinc acetate; zinc oxide, antimony oxide, stannous oxalate, zinc acetyl acetonate, calcium oxide, and manganese oxide. Titanium and zirconium catalysts are frequently used for esterification of terephthalic acid. Some typical titanium alcoholates which can be used as catalysts include tetramethyl titanates, tetraethyl titanates, tetrapropyl titanates, tetraisopropyl titanates, tetrabutyl titanates, tetrapentyl titanates, tetrahexyl titanates, and tetraoctyl titanates. The alkoxy groups on the titanium atom can all be the same or they can be different. The zirconium counterparts of the above alcoholates can be substituted in whole or in part as catalysts. Typically, the concentration of catalyst can be about 0.03 to about 1 weight percent, based on total weight of esterification reaction mixture.

Although the esterification process may be carried out in the presence of a catalyst, we have unexpectedly found that TPA has a high (i.e., about 1% at 200° C.) solubility in MCHM, which allows the esterification reaction to proceed smoothly without added catalysts. Thus, in one embodiment of the invention, the TPA and MCHM are contacted in the absence of an exogenous catalyst. Conducting the esterification reaction step in the absence of a catalyst avoids the need for additional purification steps to remove catalyst residues which can poison the hydrogenation catalysts or catalyze the formation of color bodies and other undesirable by-products in the subsequent steps of the instant process.

The process of the present invention may be carried out in a batch, semi-continuous or continuous mode. In the batch mode, for example, an agitated pressure vessel may be charged with TPA and MCHM, heated and pressurized and the esterification is carried out under reflux conditions while removing water from the reaction mixture. The high solubility of TPA in MCHM, as noted above, also allows the esterification to be conducted in a continuous mode with lower residence times and smaller reactors than would be typically used for the esterification of TPA with other alcohols. Any alcohol that is removed from the reaction mixture with the water can be recovered and fed back to the reaction vessel over the course of the process. At the conclusion of the reaction, the esterification product mixture can be used in the subsequent hydrogenation step as is or the unreacted MCHM may recovered from esterification product mixture by distillation or any conventional means known to persons skilled in the art and recycled. Continuous operation involves continuously or intermittently feeding TPA and MCHM to and continuously or intermittently removing alcohol, water and product-containing reaction mixture from a pressure vessel maintained at a predetermined temperature, pressure and liquid level. It will be apparent to those skilled in the art that other reactor schemes may be used with this invention. For example, the esterification reaction can be conducted in a plurality of reaction zones, in series, in parallel, or it may be conducted batch wise or continuously in a tubular plug flow reaction zone or series of such zones with recycle of unconsumed feed substrate materials if required. For example, the esterification reaction mixture may be fed to one or more secondary reaction vessels wherein conversion of TPA and/or TPA half-ester to the diester product is completed.

The esterification product mixture typically can comprise at least 50 weight percent of bis(4-methylcyclohexyl)methyl) terephthalate based on the total weight of the esterification product mixture, although lower concentrations may be present. Other examples of weigh percentages of bis(4-methylcyclohexyl)methyl) terephthalate in the esterification product mixture are at least 60 weight percent, at least 70 weight percent, at least 80 weight percent, and at least 90 weight percent.

The esterification product mixture can be contacted with hydrogen in a first hydrogenation zone in the presence of a catalyst effective for hydrogenation of an aromatic ring to produce a liquid effluent that comprises bis(4-methylcyclohexyl)methyl)cyclohexane-1,4-dicarboxylate, represented by formula (II):

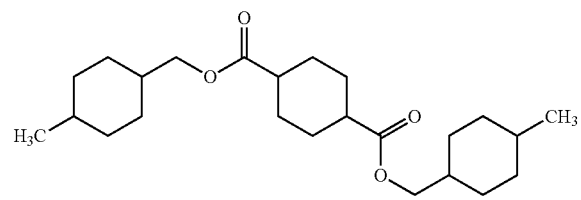

(II)

The hydrogenation of the esterification product mixture may be carried out over a temperature range of about 150° to 350° C. Generally, higher temperatures favor carbon monoxide formation and, therefore, the use of temperatures in the upper part of the range may require means for removing carbon monoxide from the hydrogenation zone such as, for example, by purging all, or substantially all, of the hydrogen effluent of the process. Other examples of temperatures for the hydrogenation of the esterification product mixture include about 160 to about 300° C., about 180 to about 300° C., about 170 to about 280° C., about 170 to about 260° C., and about 170° C. to about 240° C. The process may be operated in either an adiabatic or isothermal process.

The hydrogenation of the esterification product mixture may be performed within a pressure range of about 50 to 400 bar gauge. In another example, the pressure of the hydrogenation may range from about 50 to about 170 bar gauge.

The hydrogenation of the esterification product mixture can be carried out in a batch, semi-continuous or continuous mode using conventional chemical processing techniques. In another embodiment of the present invention, the process comprises a combination of two or more of batch, semi-continuous or continuous modes. In certain embodiments, the mode of operation may be a continuous process in which the esterification product mixture is passed over and through one or more fixed beds of catalyst in a "trickle bed" manner and all or a portion of the bis(4-methylcyclohexyl)-methyl)terephthalate is converted to bis(4-methylcyclohexyl)methyl)cyclohexane-1,4-dicarboxylate (II). For example, a portion of the effluent from one or more fixed catalyst beds, comprising bis(4-methylcyclohexyl)methyl)cyclohexane-1,4-dicarboxylate (II) may be recycled to the feed port of the reactor where it serves as a solvent for the esterification product feed. In another embodiment, the esterification product mixture may be supplied to the hydrogenation zone at a rate which will result in substantially complete conversion of the reactant to the cyclohexanedicarboxylate product. In some embodiments of the present invention, one or more inert, non-aromatic compounds, which are liquid under the operating conditions employed, may be used as a solvent or solvent mixture. Examples of suitable solvents include, but not limited to, alcohols, such as MCHM and CHDM, and other esters.

The most suitable LHSV (LHSV, liquid hourly space velocity is the unit volume of reactant fed per hour per unit volume catalyst) for the esterification product mixture feed is dependent upon the particular temperature and pressure used which, as mentioned hereinabove, can depend upon the flow rate and/or purity of the hydrogen. In trickle bed operation, the liquid hourly space velocity of the esterification product mixture feed may be in the range of about 0.1 to 10 with a preferred range of 0.5 to 5. In some embodiments the lower limit of the LHSV of the esterification product mixture feed may be 0.1 or 0.2 or 0.3 or 0.4 or 0.5 or 0.6 or 0.7 or 0.8 or 0.9 or 1.0 or 2.0 or 3.0 or 4.0 or 5.0 or 6.0 or 7.0 or 8.0 or 9.0. In some embodiments the upper limit of the LHSV of the esterification product mixture feed may be 0.2 or 0.3 or 0.4 or 0.5 or 0.6 or 0.7 or 0.8 or 0.9 or 1.0 or 2.0 or 3.0 or 4.0 or 5.0 or 6.0 or 7.0 or 8.0 or 9.0 or 10.0. The range of the LHSV of the esterification product mixture feed may be a combination of any lower limit with any upper limit listed above.

The LHSV for the total liquid flow (esterification product mixture feed plus solvent) may be in the range of 1 to 40. In some embodiments the lower limit of the LHSV of the total liquid flow may be 1.0 or 2.0 or 3.0 or 4.0 or 5.0 or 6.0 or 7.0 or 8.0 or 9.0 or 10 or 15 or 20 or 25 or 30 or 35. In some embodiments, the upper limit of the LHSV of the total liquid flow may be 2.0 or 3.0 or 4.0 or 5.0 or 6.0 or 7.0 or 8.0 or 9.0 or 10 or 15 or 20 or 25 or 30 or 35 or 40. The range of the LHSV of the total liquid flow may be a combination of any lower limit with any upper limit listed above.

The hydrogen gas used in the process may comprise fresh gas or a mixture of fresh gas and recycle gas. The hydrogen gas can be a mixture of hydrogen, optional minor amounts of components such as CO and $CO_2$, and inert gases, such as argon, nitrogen, or methane, containing at least about 70 mole % of hydrogen. For example, the hydrogen gas can contain at least 90 mole % or, in another example, at least 97 mole %, of hydrogen. The hydrogen gas may be obtained from any of the common sources well known in the art such as, for example, by partial oxidation or steam reforming of natural gas. Pressure swing absorption can be used if a high purity hydrogen gas is desired. If gas recycle is utilized in the process, then the recycle gas will normally contain minor amounts of one or more products of the hydrogenation reaction which have not been fully condensed in the product recovery stage downstream from the hydrogenation zone. Thus, when using gas recycle in the process of the invention, the gas recycle stream will typically contain a minor amount of an alkanol, e.g., MCHM. Hydrogen is typically fed to the reactor in excess of the stoichiometric quantity and normally is purged from the system. The rate of hydrogen purge is dependent on the temperature and pressure at which the process is operated.

The hydrogenation of the esterification product mixture may be catalyzed by any catalyst that is effective for the reduction of an aromatic ring. In certain embodiments for example, the catalyst can comprise a Group VIII metal (Groups 8, 9, and 10 according to IUPAC numbering) deposited on a catalyst support material comprising alumina, silica-alumina, titania, zirconia, chromium oxides, graphite, silicon carbide, or combinations thereof. Examples of the Group VIII metals that may be used include, but are not limited to, palladium, platinum, ruthenium, nickel and combinations thereof. In one embodiment of the present invention the total amount of Group VIII metal present may be about 0.1 to 10 weight percent based on the total weight of the catalyst. The lower limit of the weight percent of the Group VIII metal may be 0.1 or 0.2 or 0.3 or 04 or 0.5 or 0.6 or 0.7 or 0.8 or 0.9 or 1.0 or 2.0 or 3.0 or 4.0 or 5.0 or 6.0 or 7.0 or 8.0 or 9.0. The upper limit of the weight percent of the Group VIII metal may be 0.2 or 0.3 or 04 or 0.5 or 0.6 or 0.7 or 0.8 or 0.9 or 1.0 or 2.0 or 3.0 or 4.0 or 5.0 or 6.0 or 7.0 or 8.0 or 9.0 or 10.0. The range of the weight percent of the Group VIII metal may be any combination of any lower limit with any upper limit. For example, the catalyst can comprise palladium supported on alumina. In another embodiment of the present invention the catalyst can comprise about 0.5 to 5 weight percent palladium wherein the weight percentages are based on the total weight of the catalyst, e.g., the total weight of the support material plus the Group VIII metal. In another embodiment of the present invention the catalysts further comprise about 0.5 to 5 weight percent palladium, optionally in combination with about 0.01 to 2 weight percent nickel, ruthenium or a mixture thereof, wherein the weight percentages are based on the total weight of the catalyst, e.g., the total weight of the support material plus the metals. The catalyst may be in any conventional form such as, for example, in the form of extrudates, granules, and pellets for use in fixed-bed reactor processes and powder for slurry processes. The shape of the supports may be, but are not limit to, cylinders, spheres, stars or any type of multiple-lobe shapes. Depending on the particular support material employed and/or the method used to prepare a catalyst, the Group VIII metal may be deposited primarily on the surface of the support or distributed substantially throughout the support.

The catalysts may be prepared by conventional techniques such as impregnation of one or more Group VIII metals or Group VIII metal compounds on or into the support material. The Group VIII metals may be provided as zero valence metals or as oxidized metals in the form of compounds such as salts of inorganic or organic acids and organometallic complexes. In one embodiment, the support materials may be impregnated with one or more Group VIII metals by immersing the support material in a solution of a Group VIII metal compound in a suitable solvent such as water or an organic solvent. The support material then is dried and the metal compound is reduced to a Group VIII metal.

In one example of the invention, the esterification product mixture is contacted with hydrogen at a temperature of about 150 to about 350° C. and a pressure of about 50 to about 400 bar gauge and in the presence of a catalyst comprising palladium, platinum, nickel, ruthenium or combinations thereof deposited on a catalyst support material. In another embodiment, the esterification product mixture may be contacted with hydrogen at a temperature of about 180 to about 300° C. and a pressure of about 50 to about 170 bar gauge, in the presence of a catalyst comprising palladium, ruthenium, or combinations thereof, deposited on a catalyst support material comprising alumina, silica-alumina, titania, zirconia, chromium oxides, graphite, silicon carbide, or combinations thereof. It will be apparent to persons skilled in the art that other combinations of temperature, pressure, and catalysts may be used.

The hydrogenation of the esterification product mixture in the first hydrogenation zone produces a liquid effluent comprising bis(4-methylcyclohexyl)-methyl)cyclohexane-1,4-dicarboxylate and, optionally, (4-methylcylohexyl)methanol. The liquid effluent is contacted with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), represented by formula (III) and abbreviated to hereinafter as "MCHM-diether," and (4-methylcyclohexyl)methanol. The MCHM can comprise MCHM that was present in the esterification product mixture, released during the hydrogenation of the

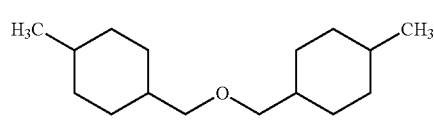

III bis(4-methylcyclohexyl)methyl)cyclohexane-1,4-dicarboxylate, and additionally produced as a by-product.

The hydrogenation conditions of pressure and temperature for the liquid effluent from the first hydrogenation zone may be varied depending not only on one another but also on the activity of the catalyst, the mode of operation, selectivity considerations, and the desired rate of conversion. The process typically is conducted at temperatures in the range of about 160° C. to about 300° C. and pressures in the range of about 40 to about 400 bar gauge (abbreviated herein as "barg"). Further examples of temperatures and pressures at which the process of the invention may be operated are about 175 to about 300° C. at about 200 to about 380 barg, and about 200 to about 250° C. at about 300 to about 350 barg. While rates and conversions generally also increase with increasing pressure, the energy costs for compression of hydrogen, as well as the increased cost of high-pressure equipment generally make the use of the lowest pressure practical advantageous.

The process of this invention may be carried out in the absence or presence of an inert solvent, i.e., a solvent for the cyclohexanedicarboxylate ester being hydrogenated which does not affect significantly the activity of the catalyst and does not react with the hydrogenation product or products. Examples of such solvents include alcohols such as ethanol and lauryl alcohol; glycols such as mono-, di- and tri-ethylene glycol; hydrocarbons such as hexane, cyclohexane, octane and decane; and aromatic ethers such as diphenyl ether, etc. It is often economically advantageous, however, to conduct the process in the absence of solvent and use the neat, molten cyclohexanedicarboxylate ester alone or as a mixture with 1,4-cyclohexanedimethanol and other hydrogenation products as the feed to the process.

The hydrogenation of the liquid effluent containing the cyclohexanedicarboxylate ester (II) may be carried out as a batch, semi-continuous or continuous process and may utilize a variety of reactor types. Examples of suitable reactor types include, but are not limited to, stirred tank, continuous stirred tank, slurry, tubular, fixed bed, and trickle bed. A plurality of reactors, stages, or hydrogenation zones may be used. For economic and operability reasons, the process is advantageously operated as a continuous process. Continuous operation may utilize a fixed bed with a larger particle size of catalyst such as, for example, granules, pellets, various multilobal shaped pellets, rings, or saddles that are well known to skilled persons in the art. As an example of a continuous process, the catalyst bed may be fixed in a high pressure, tubular or columnar reactor and the liquid effluent from the first hydrogenation zone, dissolved in an inert solvent if necessary or desired, fed continuously into the top of the bed at elevated pressure and temperature, and the crude hydrogenation product removed from the base of the reactor. Alternatively, it is possible to feed the liquid effluent containing the cyclohexanedicarboxylate ester (II) into the bottom of the bed and remove the crude product from the top of the reactor. It is also possible to use 2 or more catalyst beds or hydrogenation zones connected in parallel or in series to improve conversion, to reduce the quantity of catalyst, or to bypass a catalyst bed for periodic maintenance or catalyst removal. Another mode of continuous operation utilizes a slurry of the catalyst in an agitated pressure vessel which is equipped with a filter leg to permit continuous removal of a solution of product in unreacted ester and/or an inert solvent. In this manner a liquid reactant or reactant solution can be continuously fed to and product solution continuously removed from an agitated pressure vessel containing an agitated slurry of the catalyst.

In one example, a portion of the hydrogenation product from one or more fixed catalyst beds, comprising CHDM may be recycled to the feed port of the reactor where it serves as a solvent for the liquid effluent feed containing the cyclohexanedicarboxylate ester (II). In another embodiment, the liquid effluent feed may be supplied to the hydrogenation zone at a rate which will result in substantially complete conversion of the cyclohexanedicarboxylate ester (II) to the CHDM product. In some embodiments of the present invention, one or more inert, non-aromatic compounds, which are liquid under the operating conditions employed, may be used as a solvent or solvent mixture. Examples of suitable solvents include, but not limited to, alcohols, such as MCHM and CHDM, and other esters.

The process may be conducted in the liquid phase, the vapor phase, or as combination of the liquid and vapor phase.

For example, the process may be carried in the vapor phase as described, for example, in U.S. Pat. No. 5,395,987. In one example of a vapor phase operation, the process of the invention may be operated using vaporous feed conditions by feeding the liquid effluent containing the cyclohexanedicarboxylate ester (II) to a hydrogenation zone comprising the ester hydrogenation catalyst in essentially liquid free vaporous form. Hence, the feed stream is introduced into the hydrogenation zone at a temperature which is above the dew point of the mixture. The process may be operated so that vapor phase conditions will exist throughout the hydrogenation zone. Such a vapor phase process often has the advantage of lower operating pressures in comparison to liquid phase process which can reduce the construction and operating costs of a commercial plant.

The most suitable LHSV for the liquid effluent from the first hydrogenation zone is dependent upon the particular temperature and pressure used which, as mentioned hereinabove, can depend upon the flow rate and/or purity of the hydrogen. In trickle bed operation, the liquid hourly space velocity of the liquid effluent feed may be in the range of about 0.1 to 10 with a preferred range of 0.5 to 5. In some embodiments the lower limit of the LHSV of the liquid effluent feed may be 0.1 or 0.2 or 0.3 or 0.4 or 0.5 or 0.6 or 0.7 or 0.8 or 0.9 or 1.0 or 2.0 or 3.0 or 4.0 or 5.0 or 6.0 or 7.0 or 8.0 or 9.0. In some embodiments the upper limit of the LHSV of the liquid effluent feed may be 0.2 or 0.3 or 0.4 or 0.5 or 0.6 or 0.7 or 0.8 or 0.9 or 1.0 or 2.0 or 3.0 or 4.0 or 5.0 or 6.0 or 7.0 or 8.0 or 9.0 or 10.0. The range of the LHSV of the liquid effluent feed may be a combination of any lower limit with any upper limit listed above.

The LHSV for the total liquid flow (liquid effluent feed plus solvent) may be in the range of 1 to 40. In some embodiments the lower limit of the LHSV of the total liquid flow may be 1.0 or 2.0 or 3.0 or 4.0 or 5.0 or 6.0 or 7.0 or 8.0 or 9.0 or 10 or 15 or 20 or 25 or 30 or 35. In some embodiments the upper limit of the LHSV of the total liquid flow may be 2.0 or 3.0 or 4.0 or 5.0 or 6.0 or 7.0 or 8.0 or 9.0 or 10 or 15 or 20 or 25 or 30 or 35 or 40. The range of the LHSV of the total liquid flow may be a combination of any lower limit with any upper limit listed above.

The hydrogen gas used in the process may comprise fresh gas or a mixture of fresh gas and recycle gas. The hydrogen gas can be a mixture of hydrogen, optional minor amounts of components such as CO and $CO_2$, and inert gases, such as argon, nitrogen, or methane, containing at least about 70 mole % of hydrogen. For example, the hydrogen gas contains at least 90 mole % or, in another example, at least 97 mole %, of hydrogen. The hydrogen gas may be obtained from any of the common sources well known in the art such as, for example, by partial oxidation or steam reforming of natural gas. Pressure swing absorption can be used if a high purity hydrogen gas is desired. If gas recycle is utilized in the process, then the recycle gas will normally contain minor amounts of one or more products of the hydrogenation reaction which have not been fully condensed in the product recovery stage downstream from the hydrogenation zone. Thus, when using gas recycle in the process of the invention, the gas recycle stream will typically contain a minor amount of an alkanol, e.g., MCHM. Hydrogen is typically fed to the reactor in excess of the stoichiometric quantity and normally is purged from the system. The rate of hydrogen purge is dependent on the temperature and pressure at which the process is operated.

The hydrogenation of the cyclohexanedicarboxylate ester (III) in the liquid effluent from the first hydrogenation zone may be catalyzed by any catalyst that is effective for the reduction of esters to alcohols. Typical ester hydrogenation catalysts include copper-containing catalysts and Group VIII metal-containing catalysts. Examples of suitable copper-containing catalysts include copper-on-alumina catalysts, copper oxide, reduced copper oxide/zinc oxide catalysts, with or without a promoter, manganese promoted copper catalysts, and reduced copper chromite catalysts, with or without a promoter, while suitable Group VIII (Groups 8, 9, and 10 according to IUPAC numbering) metal-containing catalysts include platinum, palladium, nickel, and cobalt catalysts. Suitable copper oxide/zinc oxide catalyst precursors include CuO/ZnO mixtures wherein the Cu:Zn weight ratio ranges from about 0.4:1 to about 2:1. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Such promoted CuO/ZnO mixtures include the Mn-promoted CuO/ZnO precursor. Suitable copper chromite catalyst precursors include those wherein the Cu:Cr weight ratio ranges from about 0.1:1 to about 4:1, preferably from about 0.5:1 to about 4:1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. In certain embodiments for example, the catalyst can comprise a Group VIII metal deposited on a catalyst support material comprising alumina, silica-alumina, titania, zirconia, chromium oxides, graphite, silicon carbide, or combinations thereof.

The ester hydrogenation catalyst may also comprise Raney metal catalysts. The Raney metal catalyst may comprise any catalytically active metal useful for the hydrogenation of cyclohexanedicarboxylate esters to the corresponding cyclohexanedimethanols. Exemplary Raney metals include nickel, cobalt, copper, or combinations thereof. For example, the Raney metal catalyst may comprise nickel. The term "Raney metal," as used herein, means a metal produced by the "Raney" process, that is, a process in which the metal catalyst is prepared by selective removal of one or more components from an alloy and leaving the remaining metal behind as the catalyst. The Raney process is described, for example, in U.S. Pat. Nos. 1,628,190 and 6,284,703. The alloy components may be removed by any method, e.g., dissolving out by chemical means or by volatilization, etc. Typically, the Raney metal is produced by contacting an alloy of the metal, containing leachable alloying components such as aluminum, zinc, silicon, or a combination thereof, with sodium hydroxide. The catalytic metal that remains is generally in a highly active porous or finely divided state. The ratio by weight of Raney process metal to leachable alloying component in the catalyst alloy may be in the range of about 10:90 to about 90:10, as is normally the case with Raney alloys. The Raney catalyst may also comprise a metal binder which does not have to be the same as the catalytically active metal present in the catalyst alloy. Rather, it is possible to combine different Raney process metals with each other as well as with promoter metals, in the catalyst alloy and as binder, offering a further degree of freedom when adjusting the catalytic properties to the particular catalytic process. For example, the binder can be nickel, cobalt, copper, iron and, optionally, promoter metals. Generally any of the metals used for making Raney metal catalysts are suitable. The binder metal may be employed in an unreachable and unadulterated form.

In one embodiment of the process of the invention, the liquid effluent from the first hydrogenation zone is contacted with hydrogen at a temperature of 160 to about 300° C. at a pressure of about 40 to about 400 bar gauge in the presence of an ester hydrogenation catalyst comprising at least one Group VIII metal, a copper-containing catalyst, or a combination thereof. In another embodiment, the ester hydrogenation catalyst comprises copper chromite, copper oxide, Raney nickel, Raney cobalt, or combinations thereof, and is optionally promoted with zinc, barium, calcium, manganese, magnesium, nickel, ruthenium, or lanthanum. Other possible combinations of temperatures, pressures, and catalysts will be apparent to persons having ordinary skill in the art.

The hydrogenation of the effluent from the first hydrogenation zone produces a hydrogenation product comprising 1,4-cyclohexanedimethanol, 4,4'-oxybis(methylene)-bis(methylcyclohexane) (III), and (4-methylcyclohexyl)methanol that was present in the esterification product mixture, released during the hydrogenation of the bis(4-methylcyclohexyl)methyl)cyclohexane-1,4-dicarboxylate, and additionally produced as a by-product. The MCHM that is present in the hydrogenation product can comprise MCHM produced as a by-product in addition to unreacted MCHM that was present in and carried forth with the esterification product mixture and MCHM that is released by the hydrogenation of bis(4-methylcyclohexyl)methyl)cyclohexane-1,4-dicarboxylate (II). It will apparent to persons skilled in the art that the hydrogenation of 1 mole of cyclohexanedicarboxylate ester (II) will produce 2 moles of MCHM and 1 mole of CHDM. Additional MCHM is produced as a by-product of the overall hydrogenation of bis(4-methylcyclohexyl)methyl) terephthalate to CHDM. Thus, the term "by-product," as used herein in reference to the MCHM present in the hydrogenation products of the present invention, is understood to mean the MCHM that is produced in the first and second hydrogenation zones in addition to the unreacted MCHM present in esterification product mixture and the MCHM released by the hydrogenation of the cyclohexanedicarboxylate ester (II).

The MCHM in the hydrogenation product from the second hydrogenation zone can be recovered and recycled to the esterification step with terephthalic acid. For example, the MCHM in the hydrogenation product can be recovered by distillation of the hydrogenation product mixture. Fractional distillation may be employed to improve the separation of the various components of the hydrogenation product. The recovered and/or recycled MCHM may further comprise one or more additional alcohols having 4 to 20 carbon atoms in minor or major quantities. Some representative examples of additional alcohols that may be present in the recycled MCHM are 1-butanol, 2-butanol, 2-ethylhexanol, cyclohexanol, benzyl alcohol, 1-hexanol, 1-pentanol, 1-octanol, 1-nonanol, 1-decanol, or combinations thereof.

Another embodiment of our invention is a process for the preparation of 1,4-cyclohexanedimethanol from terephthalic acid, comprising:
(i). contacting terephthalic acid and (4-methylcyclohexyl)methanol in a mole ratio of alcohol to acid of about 2:1 to about 5:1, in a reaction zone at a temperature of about 220° C. to about 280° C. in the absence of a exogenous catalyst under superatmospheric pressure, while removing water from the reaction zone, to form an esterification product mixture comprising bis(4-methylcyclohexyl)methyl) terephthalate and unreacted (4-methylcyclohexyl)methanol;
(ii). contacting the esterification product mixture with hydrogen in a first hydrogenation zone in the presence of a palladium on alumina catalyst to produce a liquid effluent comprising bis(4-methylcyclohexyl)methyl)cyclohexane-1,4-dicarboxylate;
(iii). contacting the effluent from the first hydrogenation zone with hydrogen in the presence of a copper chromite catalyst in a second hydrogenation zone to produce a hydrogenation product comprising 1,4-cyclohexanedimethanol, 4,4'-oxybis-(methylene)bis(methylcyclohexane), and (4-methylcyclohexyl)methanol;
(iv). recovering the (4-methylcyclohexyl)methanol from the hydrogenation product by distillation; and
(v). recycling at least a portion of the (4-methylcyclohexyl)methanol to step (i).

For example, the hydrogenation of the effluent from the first hydrogenation zone produces a hydrogenation product comprising 1,4-cyclohexanedimethanol, 4,4'-oxybis(methylene)bis(methylcyclohexane) (III), and (4-methylcyclohexyl)methanol that was present in the esterification product mixture, released during the hydrogenation of the bis(4-methylcyclohexyl)methyl)cyclohexane-1,4-dicarboxylate, and produced as a by-product. In one embodiment of the invention, all or a portion of the (4-methylcyclohexyl)methanol that is contacted with the terephthalic acid is recycled from step (v) of the above process. In another embodiment, the amount of MCHM in the hydrogenation product of step (iii) is sufficient to satisfy the (4-methylcyclohexyl)methanol required for the esterification reaction with terephthalic acid in step (i). In yet another embodiment, the above process is a continuous process.

As described above, the MCHM may be recovered from the crude hydrogenation product from the second hydrogenation zone by distillation. It has been discovered that after distillation of the MCHM from hydrogenation product from the second hydrogenation zone, the distillation bottoms can separate into a lower layer comprising a majority of the 1,4-cyclohexanedimethanol in the distillation bottoms and an upper layer comprising a majority of the 4,4'-oxybis(methylene)bis(methylcyclohexane) (III) and other impurities in the distillation bottoms. The term "majority," is intended to have its commonly accepted meaning of "the greater part." For example, the phrase "a majority of the 4,4'-oxybis(methylene)bis(methylcyclohexane) in the distillation bottoms" is intended to mean greater than half of the total amount of the 4,4'-oxybis(methylene)-bis(methylcyclohexane) that is present in the distillation bottoms. The layers can be readily separated and CHDM recovered and purified by a simple distillation of the lower layer. The upper layer, containing the MCHM-diether and other impurities can be discarded or used in other applications. Our invention, therefore, provides a simplified method for the preparation and purification of the CHDM. Hence, another embodiment of the invention is a process for the preparation of 1,4-cyclohexanedimethanol, comprising:
(i). contacting bis(4-methylcyclohexyl)methyl) terephthalate with hydrogen in a first hydrogenation zone in the presence of a catalyst effective for hydrogenation of an aromatic ring to produce a liquid effluent comprising bis(4-methylcyclohexyl)-methyl)cyclohexane-1,4-dicarboxylate;
(ii). contacting the effluent from the first hydrogenation zone with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol;

(iii). distilling the hydrogenation product from step (ii) to recover a distillate comprising a majority of the (4-methylcyclohexyl)methanol in the hydrogenation product and a distillation bottoms comprising a majority of the 1,4-cyclohexanedimethanol, and 4,4'-oxybis(methylene)bis(methylcyclohexane) in the hydrogenation product;

(iv). allowing the distillation bottoms to form a lower layer comprising a majority of the 1,4-cyclohexanedimethanol in the distillation bottoms and a upper layer comprising a majority of the 4,4'-oxybis(methylene)bis(methylcyclohexane) in the distillation bottoms; and (v). separating the upper and lower layers of step (iv) and recovering the 1,4-cyclohexanedimethanol from the lower layer by distillation.

It should be understood that the above process comprises the various embodiments of the esterification process, hydrogenation steps, catalysts, temperature, pressure, reactor configurations, and products as described hereinabove in any combination.

For example, the bis(4-methylcyclohexyl)methyl terephthalate may be produced by esterification of terephthalic acid with (4-methylcyclohexyl)methanol and can be hydrogenated by contacting with hydrogen at a temperature of about 150 to about 350° C. and a pressure of about 50 to about 400 bar gauge in the presence of a catalyst comprising palladium, platinum, nickel, ruthenium or combinations thereof deposited on a catalyst support material. In another embodiment of our process, the bis(4-methylcyclohexyl)methyl)terephthalate may be contacted with hydrogen at a temperature of about 180 to about 250° C. and a pressure of about 50 to about 170 bar gauge, the catalyst comprises palladium, ruthenium, or combinations thereof, and the catalyst support material comprises alumina, silica-alumina, titania, zirconia, chromium oxides, graphite, silicon carbide, or combinations thereof. In still another embodiment, the catalyst in step (i) comprises palladium on alumina.

The effluent from the first hydrogenation zone can be contacted with hydrogen at a temperature of 180 to about 300° C. at a pressure of about 40 to about 400 bar gauge in the presence of an ester hydrogenation catalyst comprising at least one Group VIII metal, a copper-containing catalyst, or a combination thereof. Some representative examples of the ester hydrogenation catalyst include copper chromite, copper oxide, Raney nickel, Raney cobalt, or combinations thereof. These catalysts may be optionally promoted with zinc, barium, calcium, manganese, magnesium, nickel, ruthenium, lanthanum, titanium, or a combination thereof.

As noted above, after distillation of the MCHM from the hydrogenation product of step (ii) of the process, the distillation bottoms form an upper and lower layer wherein the lower layer comprises most of the CHDM product that was present in the distillation bottoms and the upper layer comprises the majority of the 4,4'-oxybis(methylene)bis-(methylcyclohexane) and other impurities in the distillation bottoms. For example, the lower layer comprises at least 50 weight percent of 1,4-cyclohexanedimethanol, based on the total weight of the lower layer. In another example, the upper layer comprises at least 70 weight percent of 4,4'-oxybis(methylene)bis(methylcyclohexane) based on the total weight of the upper layer. The CHDM may be recovered from the lower layer by distillation.

The MCHM that is recovered from the hydrogenation product in step (iii) of the process can be passed to a process for the preparation of bis(4-methylcyclohexyl)methyl) terephthalate by esterification of terephthalic acid. Recycling the MCHM recovered in this manner utilizes by-products that are produced in the overall CHDM process, avoids the introduction of additional materials such as, for example, alcohols that used for the preparation of terephthalate ester feedstocks, and simplifies the purification of the feedstocks and the final product. Another embodiment of our invention, therefore, is a process for the preparation of 1,4-cyclohexanedimethanol, comprising:

(i). feeding an esterification reaction product comprising bis(4-methylcyclohexyl)-methyl)terephthalate and (4-methylcyclohexyl)methanol with hydrogen to a first hydrogenation zone comprising a fixed bed of a palladium on alumina catalyst at a temperature of about 180° C. to about 250° C. and a pressure of about 50 to about 170 bar gauge to produce a liquid effluent comprising bis(4-methylcyclohexyl)-methyl cyclohexane-1,4-dicarboxylate;

(ii). feeding the liquid effluent from step (i) with hydrogen to a second hydrogenation zone comprising a fixed bed of a copper chromite catalyst at a temperature of about 180 to about 300° C. and a pressure of about 100 to about 400 bar gauge to produce a hydrogenation product comprising 1,4-cyclohexanedimethanol, (4-methylcyclohexyl)methanol, and 4,4'-oxybis(methylene)bis(methylcyclohexane);

(iii). distilling the hydrogenation product from step (ii) to recover a distillate comprising a majority of the (4-methylcyclohexyl)methanol in the hydrogenation product and a distillation bottoms comprising a majority of the 1,4-cyclohexanedimethanol and 4,4'-oxybis(methylene)bis(methylcyclohexane) in the hydrogenation product;

(iv). allowing the distillation bottoms to form a lower layer comprising a majority of the 1,4-cyclohexanedimethanol in the distillation bottoms and an upper layer comprising a majority of the 4,4'-oxybis(methylene)bis(methylcyclohexane) in the distillation bottoms;

(v). separating the upper and lower layers of step (iv) and recovering the 1,4-cyclohexanedimethanol from the lower layer by distillation; and (vi). passing the (4-methylcyclohexyl)methanol from the distillate in step (iii) to an esterification process to produce bis(4-methylcyclohexyl)methyl) terephthalate.

It is intended that the above process include the various embodiments of the esterification process, hydrogenation steps, catalysts, temperature, pressure, reactor configurations, and products as described hereinabove in any combination.

In one embodiment of the above process, for example, the lower layer comprises at least 50 weight percent of 1,4-cyclohexanedimethanol, based on the total weight of the lower layer. In another example, the upper layer contains 5 weight percent or less of 1,4-cyclohexanedimethanol, based on the total weight of the upper layer.

As noted previously, the upper layer contains the major portion of the MCHM-diether, i.e., 4,4'-oxybis(methylene)bis(methylcyclohexane) (III), that was present in the distillation bottoms. For example, the upper layer may comprise at least 70 weight percent of 4,4'-oxybis(methylene)bis(methylcyclohexane) based on the total weight of the upper layer. In another example, the upper layer can comprise at least 80 weight percent of 4,4'-oxybis(methylene)bis(methylcyclohexane) based on the total weight of the upper layer.

The MCHM that is recovered from the hydrogenation product in step (iii) of the process can be recycled by passing the recovered MCHM to a process for the preparation of bis(4-methylcyclohexyl)methyl) terephthalate by esterification of terephthalic acid. In one embodiment of the process, the amount of MCHM recovered in step (iii) is sufficient to prepare the entire esterification reaction product of step (i) that is required for the downstream CHDM process.

The esterification, hydrogenation, and purification steps described hereinabove can be combined to form an integrated process for the preparation CHDM from terephthalic acid in which the only exogenous feedstock is terephthalic acid. Yet another aspect of the instant invention, therefore, is a process for the preparation of a 1,4-cyclohexanedimethanol from terephthalic acid, comprising (i). contacting terephthalic acid and (4-methylcyclohexyl) methanol in a mole ratio of alcohol to acid of at least 2:1, in a reaction zone at a temperature of about 200° C. to about 300° C. under superatmospheric pressure, while removing water from the reaction zone, to form an esterification product mixture comprising bis(4-methylcyclohexyl)methyl)terephthalate and unreacted (4-methylcyclohexyl) methanol;

(ii). contacting the esterification product mixture with hydrogen in a first hydrogenation zone in the presence of a catalyst effective for hydrogenation of an aromatic ring to produce a liquid effluent comprising bis(4-methylcyclohexyl)-methyl)cyclohexane-1,4-dicarboxylate;

(iii). contacting the effluent from the first hydrogenation zone with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol;

(iv). distilling the hydrogenation product from step (iii) to recover a distillate comprising a majority of the (4-methylcyclohexyl)methanol in the hydrogenation product and a distillation bottoms comprising a majority of the 1,4-cyclohexanedimethanol and 4,4'-oxybis(methylene)bis(methylcyclohexane) in the hydrogenation product;

(v). allowing the distillation bottoms to form an lower layer comprising a majority of the 1,4-cyclohexanedimethanol in the distillation bottoms and a upper layer comprising a majority of the 4,4'-oxybis(methylene)bis(methylcyclohexane) in the distillation bottoms;

(vi). separating the upper and lower layers of step (v) and recovering the 1,4-cyclohexanedimethanol from the lower layer by distillation; and (vii). recycling at least a portion of the (4-methylcyclohexyl) methanol from step (iv) to step (i).

The above process includes the various embodiments of the esterification process, hydrogenation steps, catalysts, temperature, pressure, reactor configurations, and products as described hereinabove in any combination.

In one embodiment, for example, the TPA and MCHM are contacted in a reaction zone at a temperature of about 200 to about 300° C. at a pressure of about 1.4 bar gauge to about 50 bar gauge. Other examples of pressure and temperature that the esterification step may be operated at are about 220 to about 280° C. at a pressure of about 1.4 to about 21 bar gauge, and about 240 to about 270° C. at about 1.4 to about 6.9 bar gauge. The molar ratio of alcohol to acid that can be used is typically at least 2:1. Some additional examples of molar ratios of alcohol to acid in the esterification step include about 2:1 to about 9:1; about 2:1 to about 8:1; about 2:1 to about 7:1; about 2:1 to about 5:1; about 2:1 to about 4:1; and about 2:1 to about 3:1.

The removal of the water may be accomplished by any conventional means known to persons skilled in the art such as, for example, distillation, membrane separation, the use of absorbents, or combinations thereof. In one embodiment of the process of the invention, the water for the esterification is removed from the reaction zone by distillation and step (i) further comprises recovering (4-methylcyclohexyl)methanol from the esterification product mixture by distillation and recycling to the reaction zone of step (i). In one embodiment, for example, the water and/or the MCHM may be removed by distillation of a water/MCHM azeotrope, followed by separation of the water and MCHM layers. The water may then be removed from the process and the MCHM returned or recycled to the esterification reaction zone of step (i).

The esterification reaction may be carried in the presence or absence of an exogenous esterification catalyst, i.e., a catalyst other than terephthalic acid, that is added to the reaction mixture for the purpose of increasing the rate of the esterification reaction. Any esterification catalyst that is known in art may be used. For example, the TPA and MCHM can be contacted in the presence of a catalyst comprising compounds of titanium, magnesium, aluminum, boron, silicon, tin, zirconium, zinc, antimony, manganese, calcium, vanadium, sulfuric acid, p-toluene sulfonic acid, methane sulfonic acid, or phosphoric acid. Although the esterification process may be carried out in the presence of a catalyst, the reaction proceeds smoothly without added catalysts. Thus, in one embodiment of the invention, the TPA and MCHM are contacted in the absence of an exogenous catalyst. Conducting the esterification reaction step in the absence of a catalyst avoids the need for additional purification steps to remove catalyst residues which can poison the hydrogenation catalysts or catalyze the formation of color bodies and other undesirable by-products in the subsequent steps of the instant process.

The hydrogenation product from the second hydrogenation zone comprises, in addition to other products, MCHM that was present in the esterification product mixture, released during the hydrogenation of the bis(4-methylcyclohexyl)methyl)cyclohexane-1,4-dicarboxylate, and additionally produced as a by-product. All or a portion of this MCHM can be recovered, by distillation for example, and recycled to the esterification step (i) of the process of the invention. In one embodiment of the invention, all or a portion of the (4-methylcyclohexyl)methanol that is contacted with the terephthalic acid is recycled from the hydrogenation product of the second hydrogenation zone. For example, the MCHM recovered from the hydrogenation product can be combined with the MCHM recovered the esterification product mixture and recycled back to the esterification reaction. In another embodiment, all of the MCHM used in the esterification is recovered MCHM from the hydrogenation product of the second hydrogenation zone.

The process of the present invention may be carried out in a batch, semi-continuous or continuous mode. In one example, continuous operation may involve continuously or intermittently feeding TPA and MCHM to and continuously or intermittently removing alcohol, water and product-containing reaction mixture from a pressure vessel maintained at a predetermined temperature, pressure and liquid level; continuously passing the esterification product mixture to the first hydrogenation zone; continuously passing the effluent from the first hydrogenation zone to the second hydrogenation zone; continuously distilling the MCHM from the hydrogenation product of the second hydrogenation zone; continuously allowing the distillation bottoms to separate into upper and lower layers; continuously separating the layers and distilling CHDM from the lower layer; and continuously recycling the MCHM recovered from the hydrogenation product back to the esterification step. It will be apparent to those skilled in the art that other reactor schemes may be used with this invention. For example, the esterification and hydrogenation reaction steps can be conducted in a plurality of reaction zones, in series, in parallel, or it may be conducted batch wise or continuously in a tubular plug flow reaction zone or series of such zones with recycle of unconsumed feed substrate materials if required. For example, the terephthalic acid and MCHM can be contacted in a fixed bed or stirred reactor. As described hereinabove, the terephthalic acid also may be added incrementally to the reaction zone. In another example, the esterification reaction mixture may be fed to one or more secondary reaction vessels wherein conversion of TPA and/or TPA half-ester to the diester product is completed.

The esterification product mixture typically will comprise at least 50 weight percent of bis(4-methylcyclohexyl)methyl) terephthalate based on the total weight of the esterification product mixture. Other examples of weight percentages of bis(4-methylcyclohexyl)methyl)terephthalate in the esterification product mixture are at least 60 weight percent, at least 70 weight percent, at least 80 weight percent, and at least 90 weight percent.

Various embodiments of the first and second hydrogenation zone have been described above. For example, the esterification product mixture in step (ii) may be contacted with hydrogen at a temperature of about 150 to about 350° C. and a pressure of about 50 to about 400 bar gauge in the presence of a catalyst effective for hydrogenating an aromatic ring comprising palladium, platinum, nickel, ruthenium or combinations thereof deposited on a catalyst support material. In another example, the esterification product mixture in step (ii) is contacted with hydrogen at a temperature of about 180 to about 300° C. and a pressure of about 50 to about 170 bar gauge, and the catalyst effective for hydrogenating an aromatic ring comprises palladium, ruthenium, or combinations thereof, and the catalyst support material comprises alumina, silica-alumina, titania, zirconia, chromium oxides, graphite, silicon carbide, or combinations thereof. In yet another example, the catalyst effective for hydrogenating an aromatic ring comprises palladium on alumina.

The effluent from the first hydrogenation zone, comprising bis(4-methylcyclohexyl)methyl)cyclohexane-1,4-dicarboxylate (II), can be contacted with hydrogen at a temperature of 180 to about 300° C. at a pressure of about 40 to about 400 bar gauge in the presence of an ester hydrogenation catalyst comprising at least one Group VIII metal, a copper-containing catalyst, or a combination thereof. Some representative examples of ester hydrogenation catalysts include copper chromite, copper oxide, Raney nickel, Raney cobalt, or combinations thereof, and optionally promoted with zinc, barium, calcium, manganese, magnesium, nickel, ruthenium, or lanthanum.

Yet another embodiment of our novel CHDM process is a process for the preparation of a 1,4-cyclohexanedimethanol from terephthalic acid, comprising (i). contacting terephthalic acid and (4-methylcyclohexyl) methanol in a mole ratio of alcohol to acid of about 2:1 to about 5:1, in a reaction zone at a temperature of about 220° C. to about 280° C. in the absence of a exogenous catalyst under super atmospheric pressure, while distilling water from the reaction zone, to form an esterification product mixture comprising bis(4-methylcyclohexyl)methyl) terephthalate and unreacted (4-methylcyclohexyl)methanol;

(ii). recovering unreacted (4-methylcyclohexyl)methanol from esterification product mixture by distillation to form a purified esterification product mixture and recycling the unreacted (4-methylcyclohexyl)methanol to the reaction zone of step (i);

(iii). contacting the purified esterification product mixture with hydrogen in a first hydrogenation zone in the presence of a palladium on alumina catalyst to produce a liquid effluent comprising bis(4-methylcyclohexyl)methyl)cyclohexane-1,4-dicarboxylate;

(iv). contacting the effluent from the first hydrogenation zone with hydrogen in the presence of a copper chromite catalyst in a second hydrogenation zone to produce a hydrogenation product comprising 1,4-cyclohexanedimethanol, 4,4'-oxybis-(methylene)bis(methylcyclohexane), and (4-methylcyclohexyl)methanol;

(v). distilling the hydrogenation product from step (iv) to recover a distillate comprising a majority of the (4-methylcyclohexyl)methanol in the hydrogenation product and a distillation bottoms comprising a majority of the 1,4-cyclohexanedimethanol and 4,4'-oxybis(methylene)bis(methylcyclohexane) in the hydrogenation product;

(vi). allowing the distillation bottoms to form a lower layer comprising a majority of the 1,4-cyclohexanedimethanol in the distillation bottoms and an upper layer comprising a majority of the 4,4'-oxybis(methylene)bis(methylcyclohexane) in the distillation bottoms;

(vii). separating the upper and lower layers of step (vi) and recovering the 1,4-cyclohexanedimethanol from the lower layer by distillation; and (viii). recycling at least a portion of the (4-methylcyclohexyl) methanol from step (v) to the reaction zone of step (i).

It is understood that the above process comprises the various embodiments of the esterification process, hydrogenation steps, catalysts, temperature, pressure, reactor configurations, and products as described hereinabove in any combination.

In one embodiment, for example, the amount of MCHM in the hydrogenation product of step (iv) is sufficient to satisfy the MCHM required for the esterification reaction of step (i). In another embodiment, all or a portion of the MCHM that is contacted with the terephthalic acid is recycled from the hydrogenation product of the second hydrogenation zone. For example, the MCHM recovered from the hydrogenation product can be combined with the MCHM recovered the esterification product mixture and recycled back to the esterification reaction. In another embodiment, all of the MCHM used in the esterification is recovered MCHM from the hydrogenation product of the second hydrogenation zone. In yet another embodiment, the above process may be operated entirely or in part as a continuous process.

Following distillation of the hydrogenation product from the second hydrogenation zone, the distillation bottoms separates into an upper layer comprising most of the MCHM-diether and impurities that were present in the distillation bottoms and a lower layer comprising most of the CHDM that was present in the distillation bottoms. For example, the upper layer can contain 10 weight percent or less of 1,4-cyclohexanedimethanol, based on the total weight of the upper layer. In another example, the upper layer can contain 5 weight percent or less of 1,4-cyclohexanedimethanol, based on the total weight of the lower layer. In another example, the upper layer can comprise at least 70 weight percent of 4,4'-oxybis(methylene)bis(methylcyclohexane) based on the total weight of the upper layer. In still another example, the upper layer can comprise at least 80 weight percent of 4,4'-oxybis (methylene)bis(methylcyclohexane) based on the total weight of the upper layer.

The invention also includes the following embodiments that are set forth in items 1-23 below:

1. A process for the preparation of a 1,4-cyclohexanedimethanol from terephthalic acid, comprising (i). contacting terephthalic acid and (4-methylcyclohexyl) methanol in a mole ratio of alcohol to acid of at least 2:1, in a reaction zone at a temperature of about 200° C. to about 300° C. under superatmospheric pressure, while removing water from the reaction zone, to form an esterification product mixture comprising bis(4-methylcyclohexyl)methyl)terephthalate and unreacted (4-methylcyclohexyl)-methanol;

(ii). contacting the esterification product mixture with hydrogen in a first hydrogenation zone in the presence of a catalyst effective for hydrogenation of an aromatic ring to produce a liquid effluent comprising bis(4-methylcyclohexyl)-methyl)cyclohexane-1,4-dicarboxylate;

(iii). contacting the effluent from the first hydrogenation zone with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol;

(iv). distilling the hydrogenation product from step (iii) to recover a distillate comprising a majority of the (4-methylcyclohexyl)methanol in the hydrogenation product and a distillation bottoms comprising a majority of the 1,4-cyclohexanedimethanol and 4,4'-oxybis(methylene)bis(methylcyclohexane) in the hydrogenation product;

(v). allowing the distillation bottoms to form an lower layer comprising a majority of the 1,4-cyclohexanedimethanol in the distillation bottoms and a upper layer comprising a majority of the 4,4'-oxybis(methylene)bis(methylcyclohexane) in the distillation bottoms;

(vi). separating the upper and lower layers of step (v) and recovering the 1,4-cyclohexanedimethanol from the lower layer by distillation; and (vii) recycling at least a portion of the (4-methylcyclohexyl) methanol to step (i).

2. A process that includes the embodiments of item 1, wherein the temperature in step (i) is about 220° C. to about 280° C. and the pressure is about 1.4 bars gauge to about 6.9 bars gauge.

3. A process that includes the embodiments of any one of items 1-2, wherein the ratio of alcohol to acid in step (i) is about 2:1 to about 3:1.

4. A process that includes the embodiments of any one of items 1-3, wherein the water is removed from the reaction zone in step (i) by distillation and wherein step (i) further comprises recovering (4-methylcyclohexyl)methanol from the esterification product mixture by distillation and recycling to the reaction zone of step (i).

5. A process that includes the embodiments of any one of items 1-4, wherein the terephthalic acid and (4-methylcyclohexyl)methanol are contacted in the absence of an exogenous catalyst.

6. A process that includes the embodiments of any one of items 1-5, wherein all or a portion of the (4-methylcyclohexyl)methanol is contacted with the terephthalic acid is recycled from process for the preparation of CHDM by hydrogenation of bis(4-methylcyclohexyl)methyl)terephthalate.

7. A process that includes the embodiments of any one of items 1-6, wherein the process is a continuous process.

8. A process that includes the embodiments of any one of items 1-7, wherein the esterification product mixture comprises at least 70 weight percent of bis(4-methylcyclohexyl) methyl)terephthalate.

9. A process that includes the embodiments of any one of items 1-8, which comprises contacting the terephthalic acid and (4-methylcyclohexyl)methanol in a fixed bed or stirred reactor.

10. A process that includes the embodiments of any one of items 1-9, wherein the terephthalic acid is added incrementally to the reaction zone in step (i).

11. A process that includes the embodiments of any one of items 1-10, wherein the esterification product mixture in step (ii) is contacted with hydrogen at a temperature of about 150 to about 350° C. and a pressure of about 50 to about 400 bars gauge and the catalyst effective for hydrogenating an aromatic ring comprises palladium, platinum, nickel, ruthenium or combinations thereof deposited on a catalyst support material.

12. A process that includes the embodiments of any one of items 1-11, wherein the esterification product mixture in step (ii) is contacted with hydrogen at a temperature of about 180 to about 300° C. and a pressure of about 50 to about 170 bars gauge, the catalyst effective for hydrogenating an aromatic ring comprises palladium, ruthenium, or combinations thereof, and the catalyst support material comprises alumina, silica-alumina, titania, zirconia, chromium oxides, graphite, silicon carbide, or combinations thereof.

13. A process that includes the embodiments of any one of items 1-12, wherein the catalyst effective for hydrogenating an aromatic ring comprises palladium on alumina.

14. A process that includes the embodiments of any one of items 1-13, wherein the effluent from the first hydrogenation zone in step (iii) is contacted with hydrogen at a temperature of 180 to about 300° C. at a pressure of about 40 to about 400 bars gauge and the ester hydrogenation catalyst comprises at least one Group VIII metal, a copper-containing catalyst, or a combination thereof.

15. A process that includes the embodiments of any one of items 1-14, wherein the ester hydrogenation catalyst comprises copper chromite, copper oxide, Raney nickel, Raney cobalt, or combinations thereof, and optionally promoted with zinc, barium, calcium, manganese, magnesium, nickel, ruthenium, or lanthanum.

16. A process that includes the embodiments of any one of items 1-15, wherein in step (i), the terephthalic acid and (4-methylcyclohexyl)methanol are contacted at a temperature of about 220° C. to about 280° C. in the absence of a exogenous catalyst under super atmospheric pressure, while distilling water from the reaction zone; in step (ii), the unreacted (4-methylcyclohexyl)methanol is recovered from esterification product mixture by distillation to form a purified esterification product mixture and recycling the unreacted (4-methylcyclohexyl)methanol to the reaction zone of step (i); in step (iii), the purified esterification product mixture is contacted with hydrogen in a first hydrogenation zone in the presence of a palladium on alumina catalyst to produce a liquid effluent comprising bis(4-methylcyclohexyl)methyl) cyclohexane-1,4-dicarboxylate; and, in step (iv), the effluent from the first hydrogenation zone is contacted hydrogen in the presence of a copper chromite catalyst;

17. A process that includes the embodiments of items 16, wherein the amount of (4-methylcyclohexyl)methanol in the hydrogenation product is sufficient to satisfy the (4-methylcyclohexyl)methanol required for step (i).

18. A process that includes the embodiments of any one of items 16-17, wherein all or a portion of the (4-methylcyclohexyl)methanol that is contacted with the terephthalic acid is recycled from process for the preparation of CHDM by hydrogenation of bis(4-methylcyclohexyl)methyl)terephthalate.

19. A process that includes the embodiments of any one of items 16-18, wherein the process is a continuous process.

20. A process that includes the embodiments of any one of items 16-19, wherein the upper layer comprises 10 weight percent or less of 1,4-cyclohexanedimethanol, based on the total weight of the lower layer.

21. A process that includes the embodiments of any one of items 16-20, wherein the upper layer comprises 5 weight percent or less of 1,4-cyclohexanedimethanol, based on the total weight of the lower layer.

22. A process that includes the embodiments of any one of items 16-21, wherein the upper layer comprises at least 70 weight percent of 4,4'-oxybis(methylene)bis(methylcyclohexane) based on the total weight of the upper layer.

23. A process that includes the embodiments of any one of items 16-22, wherein the upper layer comprises at least 80 weight percent of 4,4'-oxybis(methylene)bis(methylcyclohexane) based on the total weight of the upper layer.

EXAMPLES

The invention is further described and illustrated by the following non-limiting examples.

Example 1

Esterification of Terephthalic Acid with (4-methylcyclohexyl)-methanol—

Terephthalic acid (10 moles) and 50 moles of (4-methylcyclohexyl)methanol ("MCHM") were charged to an oil-jacketed pilot scale batch reactor having a 2 gallon capacity, a pressure capacity of 13.5 bar gauge (196 psig), and a vacuum capacity of ~0.3 ton. The reactor had a double helical stirrer that provided moderate mixing. The unit was equipped with a side sample port allowing direct reaction mixture sampling under pressure. A reflux condenser with separate hot oil control was mounted directly to the unit head allowing partial vapor/liquid separation. A water jacketed column was attached to the reflux condenser to capture water and other liquid condensates.

The reactants were held at 5.0 bar gauge (73 psig), 260° C., and a column temperature of 150° C. with stirring for 5 hours and 20 minutes. The reaction appeared to be complete within 2 hours and 30 minutes. The column temperature increased to 156° C. and the water of reaction was removed by distillation. An NMR spectrum showed that the final conversion of terephthalic acid to bis(4-methylcyclohexyl)methyl) terephthalate to be 94% based on the amount charged. In addition to bis(4-methylcyclohexyl)methyl) terephthalate, gas chromatography/mass spectroscopy ("GC/MS") showed no free TPA within detection limits, a trace amount of the MCHM monoester of TPA, unreacted MCHM and trace amounts of other impurities.

Example 2

Esterification of Terephthalic Acid with (4-methylcyclohexyl)-methanol—

Terephthalic acid (10 moles) and MCHM (50 moles) were charged to the same apparatus described in Example 1. The reactants were held at 5.0 bar gauge (73 psig), 260° C., and a column temperature of 150° C. with stirring for 3 hours. The reactor temperature was increased to 270° C. and held for 1 hour and 30 minutes. The water of reaction was removed by distillation. The column set point was elevated to 180° C. during final hold time. The reaction appeared to be complete within 2 hours and 30 minutes. At the final conditions at 270° C., some additional MCHM condensate was captured but little to no water of reaction was collected. Proton NMR spectra showed final conversion of TPA to bis(4-methylcyclohexyl)methyl) terephthalate of 96%. In addition to bis(4-methylcyclohexyl)methyl)terephthalate, GC/MS showed a trace of TPA, a trace amount of the MCHM monoester of TPA, unreacted MCHM and trace amounts of other impurities.

Example 3

Esterification of Terephthalic Acid with (4-methylcyclohexyl)-methanol—

The esterification reaction of Example 2 was repeated with an additional 1 hour and 30 minutes of reaction time at 280° C. Proton NMR spectra showed the final conversion of TPA to bis(4-methylcyclohexyl)methyl) terephthalate of 98%. The GC/MS analysis was similar to that of Example 1.

Examples 4 and 5

Esterification of Terephthalic Acid with (4-methylcyclohexyl)-methanol—

The esterification reaction of Example 2 was repeated except that a TPA:MCHM molar ratio of 4:1 was used. The reaction appeared to be complete after 3½ hours. Proton NMR analysis indicated a TPA conversion of 98 and 96%. GS/MS analysis showed similar results to Example 2.

Examples 6 and 7

Esterification of Terephthalic Acid with (4-methylcyclohexyl)-methanol—

The esterification reaction of Example 2 was repeated except that a TPA:MCHM molar ratio of 3:1 was used. The reaction appeared to be complete after 4 hours. Proton NMR analysis indicated a TPA conversion of 92 and 97%. GS/MS analysis showed similar results to Example 2, 4, and 5.

Examples 8 and 9

Esterification of Terephthalic Acid with (4-methylcyclohexyl)methanol—

The esterification reaction of Example 2 was repeated except that a TPA:MCHM molar ratio of 2:1 was used. The reaction appeared to be complete after 4 hours. Proton NMR analysis indicated a TPA conversion of 93 and 91%. GS/MS analysis showed similar results to Example 2, 4, 5, 6, and 7.

Example 10

Comparative

Esterification of Terephthalic Acid with (4-methylcyclohexyl)methanol—

TPA (0.5 mole) and MCHM (2.0 moles) were charged to a 500 mL round-bottomed flask (TPA:MCHM molar ratio of 4:1) and stirred at 200° C. at atmospheric pressure for 48 hours. Substantial quantities of undissolved TPA remained in the reaction vessel and very little water was collected which indicated that the esterification was incomplete. No analytical data was collected.

Example 11

Comparative

Esterification of Terephthalic Acid with (4-methylcyclohexyl)methanol—

The reaction of Example 10 was repeated except that a TPA:MCHM molar ratio of 2:1 was used. The results were similar to those obtained for Example 10.

Example 12

Esterification of Terephthalic Acid with (4-methylcyclohexyl)-methanol—

Seven experiments were carried out in which TPA (2.5 moles) and MCHM (7.6 moles) were charged to an electrically heated lab scale continuous stirred tank reactor having about a 1 to 1½ gallon capacity, a pressure capacity of 13.5 bar gauge (196 psig) and equipped with an electrically traced distillation column as well as a shell and tube hot oil jacketed condenser followed by a shell and tube water jacketed condenser. The unit had a pitch blade stirrer to provide moderate mixing. Water and other condensates were captured in a water cooled vessel having a pressure rating at least equal to and in line with the reactor. The reactants were stirred together at 4.8 bar gauge (70 psig) and 260° C. for 8 hours then at 270° C. for 1 hour, and finally at 280° C. for 1 hour. The column temperature was 180° C. Analysis of the reaction product by proton NMR showed that the TPA conversion for all seven experiments was from 96 to 99%.

Example 13

Esterification of Terephthalic Acid with (4-methylcyclohexyl)-methanol—

Using the same apparatus as in Example 12, four experiments were carried out in which TPA (2.5 moles) and MCHM (5.35 moles) were stirred together at pressures ranging from 2.4 to 5.2 bar gauge (35-75 psig) for 7-8 hours. During the reaction the temperature was increased from 140 to 295° C. TPA conversion was 91 to 98% by proton NMR.

Example 14

Esterification of Terephthalic Acid with (4-methylcyclohexyl)-methanol—

Using the same apparatus as in Example 13, two experiments were carried out in which TPA (2.5 moles) and MCHM (7.1 moles) were stirred together at 2.4 bar gauge (35 psig) for 8-9 hours. During the reaction the temperature was increased from 255 to 275° C. TPA conversion was 80 to 98% by NMR. The low conversion in one experiment is believed to be from entrainment of TPA into the distillation column and poor mixing.

Example 15

Batch Hydrogenation of bis(4-methylcyclohexyl) methyl)terephthalate to bis(4-methylcyclohexyl) methyl)cyclohexane-1,4-dicarboxylate—

Bis(4-methylcyclohexyl)methyl)terephthalate (abbreviated herein as "DXT") was hydrogenated in a batch autoclave. DXT starting material was dissolved in 1,4-dimethycyclohexanedicarboxylate (abbreviated herein as "DMCD") at a concentration of 20% by weight. This mixture (220 g) was loaded into a batch autoclave with 10 g of $Pd/Al_2O_3$ catalyst and hydrogenated for 1 hour at 124.1 bar gauge (1800 psig) and 200° C. Samples of the feed material and final product material were collected and analyzed by gas chromatography ("GC") with the area % results shown in Table 1. The feed samples and reaction products and effluents were analyzed by capillary gas chromatography using an Agilent Model 6890, or equivalent gas chromatograph equipped with a thermal conductivity detector. Results are given as area percentages. The GC samples (1 microliter) were injected without dilution onto a 0.50 micron (30 m×0.25 mm) DB-WAX column using a helium carrier gas. The GC column temperature was maintained at 100° C. for 2 minutes, then programmed to 240° C. at 16° C. per minute. The final temperature of 240° C. was held for 20 minutes. The injection port used a 100:1 split ratio. In Table 1, the bis(4-methylcyclohexyl)methyl)cyclohexane-1,4-dicarboxylate hydrogenation product is abbreviated as "DXCD" and the by-product, (4-methylcyclohexyl)methyl 4-methylcyclohexanecarboxylate, is abbreviated as "MCHM ester." The conversion of DXT to DXCD was 97%. The data also shows an increase in the concentrations of MCHM and the MCHM ester.

TABLE 1

| Sample | MCHM | DMCD | MCHM Ester | DXCD | DXT | Other |
|---|---|---|---|---|---|---|
| Feed | 0.0 | 71.5 | 0.7 | 0.0 | 25.2 | 2.5 |
| Product | 0.3 | 70.6 | 1.0 | 24.7 | 0.7 | 2.7 |

The MCHM ester is thought to form as a hydrogenolysis product of DXT and therefore represents a yield loss from the process. The hydrogenolysis process also generates some MCHM.

Example 15

Batch Hydrogenation of bis(4-methylcyclohexyl) methyl)cyclohexane-1,4-dicarboxylate to 1,4-cyclohexanedimethanol ("CHDM")—

DXCD (800 g of 83% DXCD with balance MCHM and other impurities (1.7 moles of DXCD)) was hydrogenated at 4100 psi and 250° C. with 40 g of CuCr catalyst for 5 hours. Approximately 95% of the starting DXCD was converted to CHDM during this period as shown in the feed and product sample analyses in Table 2. In Table 2, the MCHM monoester of TPA is labeled "Monoester." Analyses were performed by gas chromatography and are shown as area percent.

TABLE 2

| Sample | MCHM | CHDM | MCHM Ester | Monoester | DXCD | Other |
|---|---|---|---|---|---|---|
| Feed | 6.1 | 1.0 | 0.3 | 2.7 | 82.5 | 7.4 |
| Product | 58.6 | 28.6 | 0.6 | 0 | 4.5 | 7.7 |

Both CHDM and MCHM were coproduced during the reaction, and there were no major additional byproducts observed. The CHDM cis/trans isomer ratio in the final product was 0.35, which is near the equilibrium value.

Example 16

Continuous Hydrogenation of DXT to DXCD—

The DXT material was continuously hydrogenated in a fixed bed reactor system at 124.1 bar gauge (1800 psig) and 180-225° C. The experiments were carried out in a continuous mode of operation utilizing a vertical trickle bed reactor having a length of 72 inches and an inside diameter of 1 inch as the reactor. The reactor temperature was measured with a series of 10 thermocouples inserted into the wall of the reactor. The reactor was loaded with 830 mL (519 g) of Pd/alpha-$Al_2O_3$ catalyst extrudates. The catalyst was supported by 20 mL of Penn State packing and 104 mL glass beads. An additional 400 mL of glass beads were placed on top of the catalyst.

The feed reservoir was a jacketed, 4 L graduated vessel with a bottom take-off valve. In this system, liquid feed material is added through a high pressure syringe pump into a recycle stream and then through a preheater to raise the feed temperature to the approximate reactor temperature. The reservoir, pump head, and feed lines were steam heated to prevent any feed material from freezing. Three zone heaters on the reactor were used to establish an approximate isothermal temperature profile during the experiment.

The DXT/recycle feed mixture was fed at the top of the reactor vessel along with hydrogen and contacted with the catalyst. Crude product was removed from the bottom of the reactor and fed to a level pot wherein hydrogen was separated from the crude product. From the level pot, a portion of the liquid is taken off as product with the remainder being recycled to the top of the reactor. The liquid hold-up in the reactor system was approximately 1 L. After the system reached the correct process settings (temperature, pressure, feed rate, and recycle rate), the system was held at equilibrium for the appropriate amount of time (3 full bed turnovers). Although the recycle rates were somewhat variable, the typical recycle rate was estimated to be about 11-12 L/hr.

The GC area percent compositions of the DXT feed material and hydrogenation product samples are shown in Table 3.

TABLE 3

| Sample | MCHM | CHDM | MCHM diether | MCHM Ester | DXCD | DXT | Other |
|---|---|---|---|---|---|---|---|
| Feed | 56.59 | 0.00 | 0.00 | 0.23 | 0.00 | 40.85 | 2.33 |
| Product 1 | 56.75 | 0.00 | 5.76 | 1.85 | 33.58 | 0.43 | 1.64 |
| Product 2 | 56.71 | 0.00 | 5.74 | 1.84 | 33.68 | 0.40 | 1.63 |
| Product 3 | 56.43 | 0.00 | 5.88 | 1.86 | 33.87 | 0.32 | 1.64 |
| Product 4 | 56.31 | 0.00 | 5.92 | 1.86 | 34.01 | 0.30 | 1.60 |

In these samples, most of the DXT was converted to the desired product DXCD but also formed the MCHM ester and MCHM-diether as impurities. The area percent concentration of the MCHM ester was nearly 8 times higher in the product than in the feed material. The formation of the MCHM ester is believed to occur during the hydrogenolysis of DXT and, thus, represents a yield loss to the process. Each mole of MCHM ester, however, will hydrogenate to two moles of MCHM during the hydrogenation of the ester groups. The MCHM-diether forms from the reaction of two MCHM molecules, is relatively inert to reduction and, therefore, irreversibly consumes MCHM.

Example 17

Continuous Hydrogenation of DXT to DXCD—

Using the sample reactor system as described in Example 16, a second continuous hydrogenation of DXT to DXCD was carried out using a DXT feed material that was prepared in the absence of a catalyst in order to reduce the rate of diether formation and thus limit the consumption of MCHM. In addition, the hydrogenation was conducted at 137.9 bar gauge (2000 psig) using a low acidity Pd/α-$Al_2O_3$ catalyst (750 mL, 662.8 g) and at lower temperatures (200° C.). Analyses were performed by gas chromatography and are shown as area percent in Table 4.

TABLE 4

| Sample | MCHM | CHDM | MCHM diether | MCHM ester | DXCD | DXT | Other |
|---|---|---|---|---|---|---|---|
| Feed | 11.95 | 0.00 | 0.00 | 1.00 | 0.00 | 83.46 | 3.59 |
| Product 1 | 47.83 | 0.00 | 1.33 | 1.77 | 43.00 | 1.43 | 4.65 |
| Product 2 | 54.44 | 0.00 | 1.53 | 1.64 | 37.36 | 0.94 | 4.10 |

The ratio of MCHM diether to the desired product DXCD was 0.03-0.04. These values compare favorably to the ratio of 0.17 in Example 16 (shown in Table 3) and represent approximately a fourfold decrease. Furthermore, the levels of MCHM diether and MCHM ester are nearly equal, indicating that the process is neutral with respect to MCHM.

Example 18

Hydrogenolysis of DXCD to CHDM—

The product of the first hydrogenation shown in Table 3 was reacted further to produce CHDM. This reaction was performed continuously in a trickle bed reactor at 225° C. and 344.7 bar gauge (5000 psig) using CuCr as a catalyst. The GC area percent analyses of typical product samples are shown in Table 5.

TABLE 5

| Sample | MCHM | CHDM | MCHM diether | MCHM ester | DXCD | DXT | Other |
|---|---|---|---|---|---|---|---|
| Product 1 | 81.40 | 13.07 | 3.67 | 0.13 | 0.46 | 0.02 | 1.26 |
| Product 2 | 81.43 | 13.10 | 3.68 | 0.13 | 0.48 | 0.02 | 1.16 |
| Product 3 | 81.59 | 12.93 | 3.64 | 0.13 | 0.45 | 0.02 | 1.25 |

The hydrogenolysis of DXCD produces two moles of MCHM for every mole of CHDM. The final product samples contain 12.9-13.1% CHDM dissolved in MCHM. The product material contains lower concentrations of impurities than the feed material, largely due to the reduction of the MCHM ester. More than 90% of the MCHM ester is reduced during the hydrogenolysis step, replacing some of the MCHM that was lost due to ether formation. The ether itself is relatively inert and would have to be removed in subsequent purification steps. Assuming that the area % concentrations are equivalent to weight percent, the hydrogenolysis of DXCD was nearly 100% selective to the formation of DMCD and no significant byproducts were observed during this step. The cis/trans isomer ratio of the CHDM product was 0.42.

Example 19

Purification of CHDM from Hydrogenation of DXCD—

Crude final product, comprising MCHM, CHDM, MCHM-diether, and other various byproducts was isolated from a continuous hydrogenolysis run. The crude product was analyzed by gas chromatography and shown below (trace impurities excluded for simplicity) in Table 6. Three isomers of the MCHM-diether can be seen in the gas chromatograph because of the cis/trans isomers of the cyclohexane ring:

TABLE 6

| MCHM Isomer 1 | MCHM Isomer 2 | Cis-CHDM | Trans-CHDM | MCHM diether 1 | MCHM diether 2 | MCHM diether 3 |
|---|---|---|---|---|---|---|
| 56.6% | 24.8% | 3.9% | 9.2% | 3.7% | 1.7% | 0.6% |

The total concentrations were as follows:

| | |
|---|---|
| MCHM | 81.4% |
| CHDM | 13.1% |
| MCHM diethers | 6.0% |
| Other impurities | 1.8% |

The above crude product was subjected to distillation to remove the excess MCHM. This was accomplished on a vacuum still consisting of a one-liter flask, magnetic stir bar, two 10" Penn State packed columns with feed port between the columns, a needle valve for feeding material, feed tank, vapor take-off head, magnetic valve lifter, a condenser on the vapor take-off head, a condenser for receiving material, fraction cutter, receiver, three thermometers (base, feed, take-off vapor), and magnetic stirrer. The distillation system was operated at about 10 torr and the top take-off ratio was set at 35%.

A table of the conditions, temperature profile and feed rates is included below in Table 7 and analytical results (GC, area %) are shown in Table 8.

TABLE 7

MCHM Distillation Profile

| Sample | Dist. Time (hrs) | Base Temp °C. | Feed Temp °C. | Take-off Temp °C. | Feed Vol (ml) | Take-off Vol (ml) | Take-off wt (g) |
|---|---|---|---|---|---|---|---|
| Cut 1 | 5.0 | 104 | 90 | 88 | 830 | 456 | 408.8 |
| Cut 2 | 12.0 | 154 | 90 | 86 | 490 | 479 | 428.2 |
| Cut 3 | 20.5 | 156 | 137 | 86 | 473 | 423 | 378.7 |
| Cut 4 | 27.5 | 158 | 118 | 86 | 340 | 445 | 397.0 |
| Cut 5 | 34.0 | 159 | 100 | 86 | 170 | 495 | 448.2 |
| Cut 6 | 40.5 | 158 | 100 | 86 | 290 | 450 | 406.8 |
| Cut 7 | 47.5 | 157 | 95 | 86 | 280 | 485 | 432.0 |
| Cut 8 | 53.0 | 157 | 105 | 86 | 420 | 370 | 331.8 |
| Cut 9 | 60.0 | 155 | 100 | 86 | 325 | 455 | 405.6 |
| Cut 10 | 67.0 | 156 | 135 | 86 | 630 | 450 | 404.8 |
| Cut 11 | 75.0 | 154 | 125 | 85 | 540 | 460 | 412.3 |
| Cut 12 | 81.5 | 161 | 121 | 85 | 490 | 460 | 411.7 |
| Cut 13 | 88.5 | 155 | 138 | 84 | 530 | 470 | 420.3 |
| Cut 14 | 96.0 | 158 | 146 | 103 | 0 | 462 | 415.9 |
| | | | | | | Total: | 5702.1 |

TABLE 8

Analysis of MCHM Distillation Cuts

| Sample | MCHM Isomer 1 | MCHM Isomer 2 | Cis CHDM | Trans CHDM | DMCD | MCHM diether 1 | MCHM diether 2 | MCHM diether 3 |
|---|---|---|---|---|---|---|---|---|
| Cut 1 | 56.6% | 24.8% | 3.9% | 9.2% | 0.0% | 1.4% | 1.7% | 0.6% |
| Cut 2 | 70.3% | 28.9% | 0.0% | 0.0% | 0.0% | 0.0% | 0.0% | 0.0% |
| Cut 3 | 68.4% | 30.7% | 0.0% | 0.0% | 0.0% | 0.0% | 0.0% | 0.0% |
| Cut 4 | 68.5% | 30.0% | 0.0% | 0.0% | 0.0% | 0.0% | 0.0% | 0.0% |
| Cut 5 | 68.6% | 30.0% | 0.0% | 0.0% | 0.0% | 0.0% | 0.0% | 0.0% |
| Cut 6 | 68.2% | 29.9% | 0.0% | 0.0% | 0.0% | 0.0% | 0.0% | 0.0% |
| Cut 7 | 68.2% | 29.9% | 0.0% | 0.0% | 0.0% | 0.0% | 0.0% | 0.0% |
| Cut 8 | 68.3% | 30.1% | 0.0% | 0.0% | 0.0% | 0.0% | 0.0% | 0.0% |
| Cut 9 | 68.3% | 30.1% | 0.0% | 0.0% | 0.0% | 0.0% | 0.0% | 0.0% |
| Cut 10 | 68.0% | 30.2% | 0.0% | 0.0% | 0.0% | 0.0% | 0.0% | 0.0% |
| Cut 11 | 68.4% | 30.0% | 0.0% | 0.0% | 0.0% | 0.0% | 0.0% | 0.0% |
| Cut 12 | 68.3% | 30.0% | 0.0% | 0.0% | 0.0% | 0.0% | 0.0% | 0.0% |
| Cut 13 | 68.2% | 30.0% | 0.0% | 0.0% | 0.0% | 0.0% | 0.0% | 0.0% |

As shown by analysis of the cuts from the still, very little CHDM was lost to the recovered MCHM. After the distillation was complete, two phases formed in the base, which formed a solid if allowed to cool to room temperature. The phases were separated to give 804 g of a bottom layer and 314.1 g of a top layer. The GC analyses (area %) of these layers are shown in Table 9. The sum of the area percentages for each layer was 98%.

TABLE 9

| Layer | MCHM | Cis CHDM | Trans CHDM | MCHM diethers | MCHM ester | MW 268 | MW 394 | DXCD Isomers |
|---|---|---|---|---|---|---|---|---|
| Bottom | 0.01% | 27.45% | 64.28% | 4.05% | 0.22% | 1.75% | 0.00% | 0.27% |
| Top | 0.02% | 0.70% | 1.71% | 88.91% | 2.43% | 1.04% | 0.01% | 3.15% |

The impurities labeled as "MW 268" and "MW 394" were identified by GC-MS as (4-methylcyclohexyl)methyl 4-(hydroxymethyl)cyclohexane-1-carboxylate and 1-(4-methylcyclohexyl)methyl 4-octyl cyclohexane-1,4-dicarboxylate, respectively. The composition of each layer is summarized in Table 10.

TABLE 10

| Bottom Layer | Top Layer |
|---|---|
| CHDM: 91.7% | CHDM: 2.4% |
| MCHM diether: 4.1% | MCHM dither: 88.9% |
| 4.2% other impurities | 8.7% other impurities |

The bottom layer was distilled to remove MCHM diether using a two-liter round bottom flask, stir bar, thermometer, 10" Penn state packed column, magnetic take-off head, condenser, fraction cutter, and take-off receiver. The base was charged with the bottom layer from the phase-separated mixture. Heat and vacuum was applied to the equipment and the column was operated as summarized in Table 11:

TABLE 11

Distillation Profile for Bottom Layer

| Dist. Time (hrs) | Base Temp ° C. | Take-off Temp ° C. | Take-off Vol (ml) | Vacuum torr | Take-off wt (g) |
|---|---|---|---|---|---|
| 0.0 | 169 | 142 | 0 | 10 | |
| 0.5 | 160 | 144 | 2 | 10 | |
| 1.0 | 160 | 145 | 3 | 10 | |
| 1.5 | 162 | 145 | 12 | 10 | |
| 2.0 | 163 | 147 | 15 | 10 | |
| 2.5 | 164 | 148 | 18 | 10 | 14.8 |
| 3.0 | 160 | 143 | 6 | 10 | |
| 3.5 | 161 | 144 | 7 | 10 | |
| 4.0 | 167 | 146 | 18 | 10 | |
| 4.5 | 167 | 147 | 33 | 10 | |
| 5.0 | 167 | 148 | 39 | 10 | 29.5 |
| 5.5 | 165 | 151 | 8 | 10 | |
| 6.5 | 165 | 158 | 10 | 10 | |
| 7.0 | 166 | 160 | 11 | 10 | |
| 7.5 | 168 | 162 | 12 | 10 | |
| 8.0 | 169 | 164 | 12 | 10 | |
| 8.5 | 166 | 160 | 13 | 10 | |
| 9.0 | 166 | 160 | 30.8 | 10 | 30.8 |

After the ether removal step, the magnetic take-off head was removed and replaced with a 3" Vigreux column and heat tape applied to take-off line to keep CHDM melted until collected. The distillation profile is shown in Table 12 and an analysis of the distillation cuts is provided in Table 13.

TABLE 12

| Sample | Time (hrs) | Base Temp ° C. | Take-off Temp ° C. | Take-off Vol (ml) | Pressure (torr) | Take-off (g) |
|---|---|---|---|---|---|---|
| Cut 1 | 0.0 | 162 | 25 | 0 | 10 | |
| Cut 1 | 0.5 | 165 | 155 | 70 | 10 | |
| Cut 1 | 1.0 | 165 | 155 | 110 | 10 | |
| Cut 1 | 1.5 | 166 | 155 | 175 | 10 | |
| Cut 1 | 1.8 | 166 | 155 | 220 | 10 | 226.1 |
| Cut 2 | 2.0 | 166 | 156 | 40 | 10 | |
| Cut 2 | 2.5 | 166 | 156 | 110 | 10 | |
| Cut 2 | 3.0 | 166 | 156 | 185 | 10 | |
| Cut 2 | 3.3 | 166 | 156 | 219 | 10 | 221.8 |
| Cut 3 | 3.5 | 166 | 156 | 35 | 10 | |
| Cut 3 | 4.2 | 166 | 156 | 150 | 10 | 150.6 |
| Residue | | | | | | 110.9 |

TABLE 13

Analysis of Distillation Cuts

| Sample | MCHM | Cis CHDM | Trans CHDM | MCHM diether | MCHM ester | MW 268 | MW 394 | DXCD |
|---|---|---|---|---|---|---|---|---|
| Cut 1 | 0.08% | 25.81% | 73.04% | 0.00% | 0.05% | 0.03% | 0.00% | 0.00% |
| Cut 2 | 0.03% | 28.65% | 70.52% | 0.00% | 0.00% | 0.01% | 0.00% | 0.00% |
| Cut 3 | 0.05% | 32.53% | 66.71% | 0.10% | 0.00% | 0.02% | 0.00% | 0.00% |
| Residue | 0.11% | 30.57% | 42.12% | 0.01% | 0.00% | 11.43% | 0.00% | 1.12% |

We claim:

1. A process for the preparation of a 1,4-cyclohexanedimethanol from terephthalic acid, comprising:
    (i). contacting terephthalic acid and (4-methylcyclohexyl)methanol in a mole ratio of alcohol to acid of at least 2:1, in a reaction zone at a temperature of about 200° C. to about 300° C. under superatmospheric pressure, while removing water from the reaction zone, to form an esterification product mixture comprising bis(4-methylcyclohexyl)methyl) terephthalate and unreacted (4-methylcyclohexyl)methanol;
    (ii). contacting the esterification product mixture with hydrogen in a first hydrogenation zone in the presence of a catalyst effective for hydrogenation of an aromatic ring to produce a liquid effluent comprising bis(4-methylcyclohexyl)methyl)cyclohexane-1,4-dicarboxylate;
    (iii). contacting the effluent from the first hydrogenation zone with hydrogen in the presence of an ester hydrogenation catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol;
    (iv). distilling the hydrogenation product from step (iii) to recover a distillate comprising a majority of the (4-methylcyclohexyl)methanol in the hydrogenation product and a distillation bottoms comprising a majority of the 1,4-cyclohexanedimethanol and 4,4'-oxybis(methylene)bis(methylcyclohexane) in the hydrogenation product;

(v). allowing the distillation bottoms to form an lower layer comprising a majority of the 1,4-cyclohexanedimethanol in the distillation bottoms and a upper layer comprising a majority of the 4,4'-oxybis(methylene)-bis (methylcyclohexane) in the distillation bottoms;

(vi). separating the upper and lower layers of step (v) and recovering the 1,4-cyclohexanedimethanol from the lower layer by distillation; and (vii). recycling at least a portion of the (4-methylcyclohexyl)methanol to step (i).

2. The process according to claim 1, wherein the temperature in step (i) is about 220° C. to about 280° C. and the pressure is about 1.4 bars gauge to about 6.9 bars gauge.

3. The process according to claim 1, wherein the ratio of alcohol to acid in step (i) is about 2:1 to about 3:1.

4. The process according to claim 1, wherein the water is removed from the reaction zone in step (i) by distillation and wherein step (i) further comprises recovering (4-methylcyclohexyl)methanol from the esterification product mixture by distillation and recycling to the reaction zone of step (i).

5. The process according to claim 1, wherein the terephthalic acid and (4-methylcyclohexyl)methanol are contacted in the absence of an exogenous catalyst.

6. The process according to claim 1, wherein all or a portion of the (4-methylcyclohexyl)methanol is contacted with the terephthalic acid is recycled from process for the preparation of CHDM by hydrogenation of bis(4-methylcyclohexyl)methyl)terephthalate.

7. The process according to claim 1, which is a continuous process.

8. The process according to claim 1, wherein the esterification product mixture comprises at least 70 weight percent of bis(4-methylcyclohexyl)methyl)terephthalate.

9. The process according to claim 1, which comprises contacting the terephthalic acid and (4-methylcyclohexyl)methanol in a fixed bed or stirred reactor.

10. The process according to claim 1, wherein the terephthalic acid is added incrementally to the reaction zone.

11. The process according to claim 1, wherein the esterification product mixture in step (ii) is contacted with hydrogen at a temperature of about 150 to about 350° C. and a pressure of about 50 to about 400 bars gauge and the catalyst effective for hydrogenating an aromatic ring comprises palladium, platinum, nickel, ruthenium or combinations thereof deposited on a catalyst support material.

12. The process according to claim 1, wherein the esterification product mixture in step (ii) is contacted with hydrogen at a temperature of about 180 to about 300° C. and a pressure of about 50 to about 170 bars gauge, the catalyst effective for hydrogenating an aromatic ring comprises palladium, ruthenium, or combinations thereof, and the catalyst support material comprises alumina, silica-alumina, titania, zirconia, chromium oxides, graphite, silicon carbide, or combinations thereof.

13. The process according to claim 1, wherein the catalyst effective for hydrogenating an aromatic ring comprises palladium on alumina.

14. The process according to claim 1 wherein the effluent from the first hydrogenation zone in step (iii) is contacted with hydrogen at a temperature of 180 to about 300° C. at a pressure of about 40 to about 400 bars gauge and the ester hydrogenation catalyst comprises at least one Group VIII metal, a copper-containing catalyst, or a combination thereof.

15. The process according to claim 1, wherein the ester hydrogenation catalyst comprises copper chromite, copper oxide, Raney nickel, Raney cobalt, or combinations thereof, and optionally promoted with zinc, barium, calcium, manganese, magnesium, nickel, ruthenium, or lanthanum.

16. A process for the preparation of a 1,4-cyclohexanedimethanol from terephthalic acid, comprising (i). contacting terephthalic acid and (4-methylcyclohexyl)methanol in a mole ratio of alcohol to acid of about 2:1 to about 5:1, in a reaction zone at a temperature of about 220° C. to about 280° C. in the absence of a exogenous catalyst under super atmospheric pressure, while distilling water from the reaction zone, to form an esterification product mixture comprising bis(4-methylcyclohexyl)methyl)terephthalate and unreacted (4-methylcyclohexyl)methanol;

(ii). recovering unreacted (4-methylcyclohexyl)methanol from esterification product mixture by distillation to form a purified esterification product mixture and recycling the unreacted (4-methylcyclohexyl)methanol to the reaction zone of step (i);

(iii). contacting the purified esterification product mixture with hydrogen in a first hydrogenation zone in the presence of a palladium on alumina catalyst to produce a liquid effluent comprising bis(4-methylcyclohexyl)methyl)cyclohexane-1,4-dicarboxylate;

(iv). contacting the effluent from the first hydrogenation zone with hydrogen in the presence of a copper chromite catalyst in a second hydrogenation zone to produce a hydrogenation product comprising 1,4-cyclohexanedimethanol, 4,4'-oxybis(methylene)bis(methylcyclohexane), and (4-methylcyclohexyl)methanol;

(v). distilling the hydrogenation product from step (iv) to recover a distillate comprising a majority of the (4-methylcyclohexyl)methanol in the hydrogenation product and a distillation bottoms comprising a majority of the 1,4-cyclohexanedimethanol and 4,4'-oxybis(methylene)bis(methylcyclohexane) in the hydrogenation product;

(vi). allowing the distillation bottoms to form a lower layer comprising a majority of the 1,4-cyclohexanedimethanol in the distillation bottoms and an upper layer comprising a majority of the 4,4'-oxybis(methylene)-bis (methylcyclohexane) in the distillation bottoms;

(vii). separating the upper and lower layers of step (vi) and recovering the 1,4-cyclohexanedimethanol from the lower layer by distillation; and (viii) recycling at least a portion of the (4-methylcyclohexyl)methanol from step (v) to the reaction zone of step (i).

17. The process according to claim 16, wherein the amount of (4-methylcyclohexyl)-methanol in the hydrogenation product is sufficient to satisfy the (4-methylcyclohexyl)methanol required for step (i).

18. The process according to claim 16, wherein all or a portion of the (4-methylcyclohexyl)methanol that is contacted with the terephthalic acid is recycled from a process for the preparation of CHDM by hydrogenation of bis(4-methylcyclohexyl)methyl)terephthalate.

19. The process according to claim 16, which is a continuous process.

20. The process according to claim 16, wherein the upper layer comprises 10 weight percent or less of 1,4-cyclohexanedimethanol, based on the total weight of the lower layer.

21. The process according to claim 16, wherein the upper layer comprises 5 weight percent or less of 1,4-cyclohexanedimethanol, based on the total weight of the lower layer.

22. The process according to claim 16, wherein the upper layer comprises at least 70 weight percent of 4,4'-oxybis(methylene)bis(methylcyclohexane) based on the total weight of the upper layer.

23. The process according to claim 16, wherein the upper layer comprises at least 80 weight percent of 4,4'-oxybis(methylene)bis(methylcyclohexane) based on the total weight of the upper layer.

\* \* \* \* \*